US009532987B2

(12) United States Patent
Belvin et al.

(10) Patent No.: US 9,532,987 B2
(45) Date of Patent: Jan. 3, 2017

(54) USE OF A COMBINATION OF A MEK INHIBITOR AND AN ERK INHIBITOR FOR TREATMENT OF HYPERPROLIFERATIVE DISEASES

(71) Applicant: Genentech, Inc., South San Francisco, CA (US)

(72) Inventors: Marcia Belvin, Albany, CA (US); John Moffat, San Francisco, CA (US); Mark Merchant, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 22 days.

(21) Appl. No.: 14/473,311

(22) Filed: Aug. 29, 2014

(65) Prior Publication Data
US 2015/0111869 A1  Apr. 23, 2015

Related U.S. Application Data

(60) Provisional application No. 61/874,206, filed on Sep. 5, 2013.

(51) Int. Cl.
| *A61K 31/506* | (2006.01) |
| *A61K 31/397* | (2006.01) |
| *A61K 31/435* | (2006.01) |
| *A61K 31/437* | (2006.01) |
| *A61K 31/5025* | (2006.01) |

(52) U.S. Cl.
CPC ........... *A61K 31/506* (2013.01); *A61K 31/397* (2013.01); *A61K 31/435* (2013.01); *A61K 31/437* (2013.01); *A61K 31/5025* (2013.01)

(58) Field of Classification Search
CPC  A61K 2300/00; A61K 31/397; A61K 31/435; A61K 31/437; A61K 31/5025; A61K 31/506
See application file for complete search history.

(56) References Cited

U.S. PATENT DOCUMENTS

| 7,855,216 | B2 | 12/2010 | Goodacre et al. |
| 7,893,085 | B2 | 2/2011  | Savy et al. |
| 7,915,250 | B2 | 3/2011  | Aay et al. |
| 7,923,456 | B2 | 4/2011  | Price et al. |
| 7,999,006 | B2 | 8/2011  | Lamb et al. |
| 8,258,152 | B2 | 9/2012  | Dyke et al. |
| 8,288,408 | B2 | 10/2012 | Price et al. |
| 8,293,763 | B2 | 10/2012 | Price et al. |
| 8,362,002 | B2 | 1/2013  | Aay et al. |
| 8,486,963 | B2 | 7/2013  | Price et al. |
| 8,492,427 | B2 | 7/2013  | Gancia et al. |
| 8,697,715 | B2 | 4/2014  | Blake et al. |
| 8,722,657 | B2 | 5/2014  | Catron et al. |
| 8,841,462 | B2 | 9/2014  | Heald et al. |
| 9,187,462 | B2 | 11/2015 | Blake et al. |
| 9,206,174 | B2 | 12/2015 | Heald et al. |
| 2008/0081821 | A1 | 4/2008  | Savy et al. |
| 2008/0085886 | A1 | 4/2008  | Savy et al. |
| 2008/0166359 | A1 | 7/2008  | Lamb et al. |
| 2008/0242655 | A1 | 10/2008 | Goodacre et al. |
| 2009/0156576 | A1 | 6/2009  | Aay et al. |
| 2010/0004269 | A1 | 1/2010  | Price et al. |
| 2010/0216768 | A1 | 8/2010  | Dyke et al. |
| 2010/0249096 | A1 | 9/2010  | Aay et al. |
| 2010/0280063 | A1 | 11/2010 | Price et al. |
| 2011/0086837 | A1 | 4/2011  | Belvin et al. |
| 2011/0124622 | A1 | 5/2011  | Gancia et al. |
| 2011/0142826 | A1 | 6/2011  | Price et al. |
| 2011/0158990 | A1 | 6/2011  | Price et al. |
| 2011/0190257 | A1 | 8/2011  | Heald et al. |
| 2011/0263558 | A1 | 10/2011 | Aay et al. |
| 2012/0214828 | A1 | 8/2012  | Hatzivassiliou et al. |
| 2012/0309765 | A1 | 12/2012 | Price et al. |
| 2013/0150584 | A1 | 6/2013  | Price et al. |
| 2013/0252934 | A1 | 9/2013  | Blake et al. |
| 2013/0267517 | A1 | 10/2013 | Guo et al. |
| 2013/0338140 | A1 | 12/2013 | Blake et al. |
| 2014/0066453 | A1 | 3/2014  | Blake et al. |
| 2014/0093568 | A1 | 4/2014  | Bray et al. |
| 2014/0249127 | A1 | 9/2014  | Blake et al. |
| 2015/0087644 | A1 | 3/2015  | Flohr et al. |
| 2015/0141399 | A1 | 5/2015  | Aay et al. |
| 2015/0164895 | A1 | 6/2015  | Hatzivassiliou et al. |
| 2015/0182537 | A1 | 7/2015  | Kolesnikov et al. |
| 2015/0210668 | A1 | 7/2015  | Naganathan et al. |
| 2015/0218176 | A1 | 8/2015  | Burdick et al. |
| 2016/0052921 | A1 | 2/2016  | Guo et al. |

FOREIGN PATENT DOCUMENTS

| WO | 2007/044515 A1 | 4/2007 |
| WO | 2008/024724 A1 | 2/2008 |
| WO | 2008/024725 A1 | 2/2008 |
| WO | 2008/067481 A1 | 6/2008 |

(Continued)

OTHER PUBLICATIONS

Anderson (Chem and Biol 10:787-797, 2003.*
Thiel (Nature Biotechnol 2:513-519, 2004.*
Tan et al. (World j Gastroenterol, 2012, 18, pp. 5171-5180).*
International Search Report for PCT/EP2014/068776.
Written Opinion of the International Searching Authority for PCT/EP2014/068776.
Eric W. Joseph et al., "The RAF inhibitor PLX4032 inhibits ERK signaling and tumor cell proliferation in a V600E BRAF-selective manner" Proceedings of the National Academy of Sciences 107:14903-14908 (Aug. 17, 2010).

(Continued)

*Primary Examiner* — Savitha Rao

(57) ABSTRACT

The invention provides combinations comprising a MEK inhibitor (such as GDC-0973 or GDC-0623), or a pharmaceutically acceptable salt thereof and an ERK inhibitor (such as GDC-0994). The combinations are particularly useful for treating hyperproliferative disorders, such as cancer.

8 Claims, 21 Drawing Sheets

(56) References Cited

FOREIGN PATENT DOCUMENTS

| WO | 2008/076415 | A1 | 6/2008 |
| WO | 2008/157179 | A2 | 12/2008 |
| WO | 2009/082687 | A1 | 7/2009 |
| WO | 2009/085980 | A1 | 7/2009 |
| WO | 2009/085983 | A1 | 7/2009 |
| WO | 2010/003022 | A1 | 1/2010 |
| WO | 2010/003025 | A1 | 1/2010 |
| WO | 2011/028540 | | 3/2011 |
| WO | 2011/054620 | | 5/2011 |
| WO | 2012/118850 | A1 | 9/2012 |
| WO | 2012/145503 | A1 | 10/2012 |
| WO | 2013/020062 | A1 | 2/2013 |
| WO | 2013/130976 | A1 | 9/2013 |
| WO | 2014/027056 | A1 | 2/2014 |
| WO | 2014/036015 | A1 | 3/2014 |
| WO | 2014/059422 | A1 | 4/2014 |
| WO | 2014/060395 | A1 | 4/2014 |
| WO | 2015/085007 | A1 | 6/2015 |
| WO | 2015/103133 | A1 | 7/2015 |
| WO | 2015/103137 | A1 | 7/2015 |
| WO | 2015/154674 | A1 | 10/2015 |

OTHER PUBLICATIONS

Hatzivassiliou G. et al., "ERK Inhibition Overcomes Acquired Resistance to MEK Inhibitors" Molecular Cancer Therapeutics 2012 American Association for Cancer Research 11:1143-1154 (Mar. 8, 2012).

Hung Huynh, "AZD6244 enhances the anti-tumor activity of sorafenib in ectopic and orthotopic models of human hepatocellular carcinoma (HCC)" Journal of Hepatalogy 52:79-87 (2010).

Liu et al., "Sorafenib blocks the RAF/MEK/ERK pathway, inhibits tumor angiogenesis, and induces tumor cell apoptosis in hepatocellular carcinoma model PLC/PRF/5" Cancer Research 66(24):11851-11858 (2006).

Natalia V. Bogatcheva et al., "Mechanism of fluoride-induced MAP kinase activation in pulmonary artery endothelial cells" Am J Physiol Lung Cell Mol Physiol 290:L1139-L1145 (Jan. 13, 2006).

* cited by examiner

Combination Efficacy at Tolerated Doses is Observed with GDC-0973 and GDC-0994 Combinations in HCT116 Cells.

| %TGI (Lower, Upper CI) | GDC-0994 (mg/kg) | | | | | | |
|---|---|---|---|---|---|---|---|
| GDC-0973 (mg/kg) | 0 | 25 | 37.5 | 50 | 62.5 | 75 | 150 |
| 0 | 0 (0,0) | 38 (-49,80) | n.d. | 79 (52,99) | n.d. | 66 (22,87) | 104 (90,119) |
| 1 | 48 (-5,77) | 57 (11,81) | n.d. | 73 (39,90) | n.d. | 74 (42,95) | n.d. |
| 2 | n.d. | n.d. | 81 (53,97) | n.d. | 93 (72,110) | 0 (0,0) | n.d. |
| 3 | 41 (-18,72) | 73 (43,91) | n.d. | 68 (35,89) | n.d. | 97 (79,113) | n.d. |
| 5 | 62 (19,86) | 85 (61,102) | 80 (55,98) | n.d. | 98 (80,113) | 112 (100,131) | n.d. |
| 7.5 | 72 (39,92) | 100 (86,116) | n.d. | 111 (99,126) | n.d. | 117 (106,138) | n.d. |
| 10 | 87 (68,101) | n.d. | n.d. | n.d. | n.d. | n.d. | n.d. |

- Grey cells indicate the best combination efficacy for a tolerated regimen
- Black cells indicates non-tolerated combinations
- Dosing was daily (QD) oral gavage (PO)
- Numbers represent % Tumor Growth Inhibition (%TGI) relative to vehicle (0,0) +/- 95th percent confidence intervals (CI).

n.d. = not determined

FIG. 9

USE OF A COMBINATION OF A MEK INHIBITOR AND AN ERK INHIBITOR FOR TREATMENT OF HYPERPROLIFERATIVE DISEASES

FIELD OF THE INVENTION

The invention relates generally to pharmaceutical combinations of MEK inhibitors (MEKi) and ERK inhibitor (ERKi) with activity against hyperproliferative disorders such as cancer. The invention also relates to methods of using the compounds for treatment of mammals.

BACKGROUND OF THE INVENTION

The RAS/RAF/MEK/ERK pathway is activated in more than 30% of human cancers, most commonly via mutation in the K-ras oncogene and also via mutations in BRAF. The pathway has therefore attracted significant interest as a therapeutic target or cancer (P. J. Roberts and C. J. Der, *Oncogene* 2007 26:3291-310)). Efforts to target RAS directly have not been successful to date, but recent clinical trials with BRAF and mitogen-activated extracellular signal-regulated kinase (MEK) inhibitors have suggested targeting these downstream RAS effectors holds promise in the treatment of cancers harboring oncogenic mutations in the pathway (K. T. Flaherty et al., *Curr. Opin. Oncol.* 2010 22:178-83). Although clinical responses and antitumor activity can be impressive, particularly for BRAF inhibitors in BRAF mutant melanoma, the majority of patients ultimately develop clinical resistance and progressive disease (Flaherty, supra; D. B. Solit and N. Rosen, *N. Engl. J. Med.* 2011 364:772-4). Preclinical studies have identified multiple mechanisms of acquired resistance to BRAF inhibitors, including, switching between RAF isoforms (J. Villaneuva et al., *Cancer Cell* 2010 18:683-95), upregulation of RTK or NRAS signaling (R. Nazarian et al., *Nature* 2010 468:973-7), and reactivation of mitogen-activated kinase (MAPK) signaling via COT activation (C. M. Johannessen et al., *Nature* 2010 468:968-72) or a MEK kinase activating mutation (N. Wagle et al., *J. Clin. Oncol.* 2011 29:3085-96). Similarly preclinical studies have identified distinct mechanisms by which cell acquires resistance to MEK inhibition, including amplification of mutant BRAF (R. B. Corcorran et al., *Sci. Signal* 2011 3:ra84), STAT3 upregulation (B. Dai et al., *Cancer Res.* 2011 71:3658-68), or mutations in the allosteric pocket of MEK that can directly binding of inhibitors to the MEK kinase activity (H. Wang et al., *Cancer Res.* 2011 71:5535-45; C. M. Emery et al., *Proc. Nat. Acad. Sci. USA* 2009 106:20411-6). MEK mutations have been described in tumors samples from patients treated with MEK (Emera, supra) or BRAF (Wagle supra) inhibitors, showing clinical relevance.

While selective ERK1/2 inhibitors have been reported and are current in clinical development, in comparison with RAF and MEK inhibitors, the identification and development of small molecule inhibitors against ERK1/2 that act directly downstream of MEK, has lagged behind.

SUMMARY OF THE INVENTION

The invention relates generally to synergistic combinations of MEK inhibitors and ERK inhibitors with anti-cancer activity which administered in combination inhibit the growth of cancer-cells. The combinations and methods of the invention may be useful in the treatment of hyperproliferative disorders such as cancer. The compositions may inhibit tumor growth in mammals and may be useful for treating human cancer patients.

In one aspect, the invention includes a method for the treatment of a hyperproliferative disorder comprising administering a therapeutic combination as a combined formulation or alternation to a mammal, wherein the therapeutic combination comprises a therapeutically effective amount of a MEKi compound and a therapeutically effective amount of an ERKi. In one aspect of the present invention the ERK inhibitor is selected from (S)-1-(1-(4-chloro-3-fluorophenyl)-2-hydroxyethyl)-4-(2-((1-methyl-1H-pyrazol-5-yl)amino)pyrimidin-4-yl)pyridin-2(1H)-one (Ia, GDC-0994), 4-(3-((ethyldimethylsilyl)methyl)-[1,2,4]triazolo[4,3-a]pyridin-7-yl)-N-(1-methyl-1H-pyrazol-5-yl)pyrimidin-2-amine (Ib), (S)-4-(3-(2-(4-chlorophenyl)-2-methoxyethyl)-[1,2,4]triazolo[4,3-b]pyridazin-7-yl)-N-(1-methyl-1H-pyrazol-5-yl)pyrimidin-2-amine (Ic) or (S)—N-(1-methyl-1H-pyrazol-5-yl)-4-(3-(2-methylbutyl)-[1,2,3]triazolo[1,5-a]pyridin-6-yl)pyrimidin-2-amine (Id) and the MEK inhibitor is cobimetinib (II, GDC-0973) or 5-((2-fluoro-4-iodophenyl)amino)-N-(2-hydroxyethoxyl)imidazo[1,5-a]pyridine-6-carboxamide (IIa, GDC-0623). In another aspect of the invention, The MEK inhibitor is (II) and the ERK inhibitor is GDC-0994 (Ia).

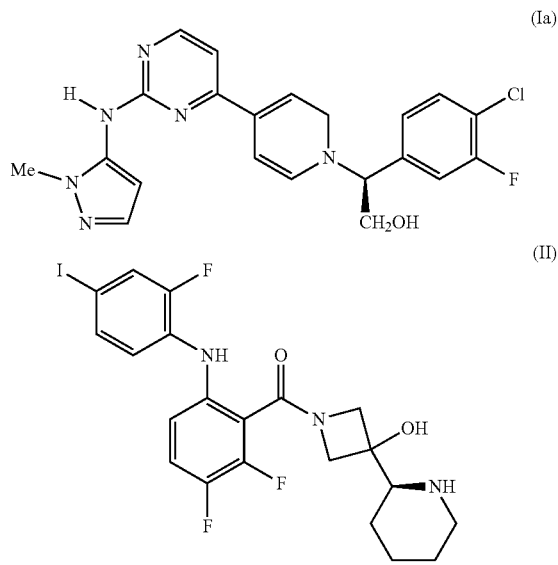

Another aspect of the invention provides a method of treating a hyperproliferative disease or disorder modulated by RAS/RAF/MEK/ERK kinases comprising administering to a mammal in need thereof effective amounts of a compound of Formula Ia-Id and a compound of formula II or IIa. The compounds of Formula Ia-Id and II or IIa may be co-formulated for administration in a combination as a pharmaceutical composition or they may be administered separately in alternation (sequentially) as a therapeutic combination.

Another aspect of the invention provides methods of treating a hyperproliferative disorder, comprising administering to a mammal in need thereof effective amounts of a compound of Formula Ia-Id, a compound of formula II (GDC-0973) or IIa and another chemotherapeutic agent.

Another aspect of the invention includes articles of manufacture or kits comprising a compound of Formula Ia-Id and a compound of formula (GDC-0973) or IIa, a container, and optionally a package insert or label indicating a treatment.

Another aspect of the invention includes a method for determining compounds to be used in combination for the treatment of cancer comprising: a) administering a therapeutic combination of MEKi and a ERKi to an in vitro tumor cell line with a Kras mutation, and b) measuring a synergistic or non-synergistic effect.

Fluorescence microscope images were acquired with a Perkin Elmer Opera high-content imaging system. The fraction of EdU-labeled cells relative to total number of cells was determined using Acapella image-analysis software.

To determine possible interactions between the drug treatments the observed response for each pair of concentrations was compared with the expected response for two non-interacting agents based on Bliss additivity ($F_{a+b}=F_a+F_b-F_a*F_b$ where Fa and Fb are the fractional effects of agents a and b). The difference between observed and predicted fractional effect is referred to as the Bliss excess.

Figure 5:
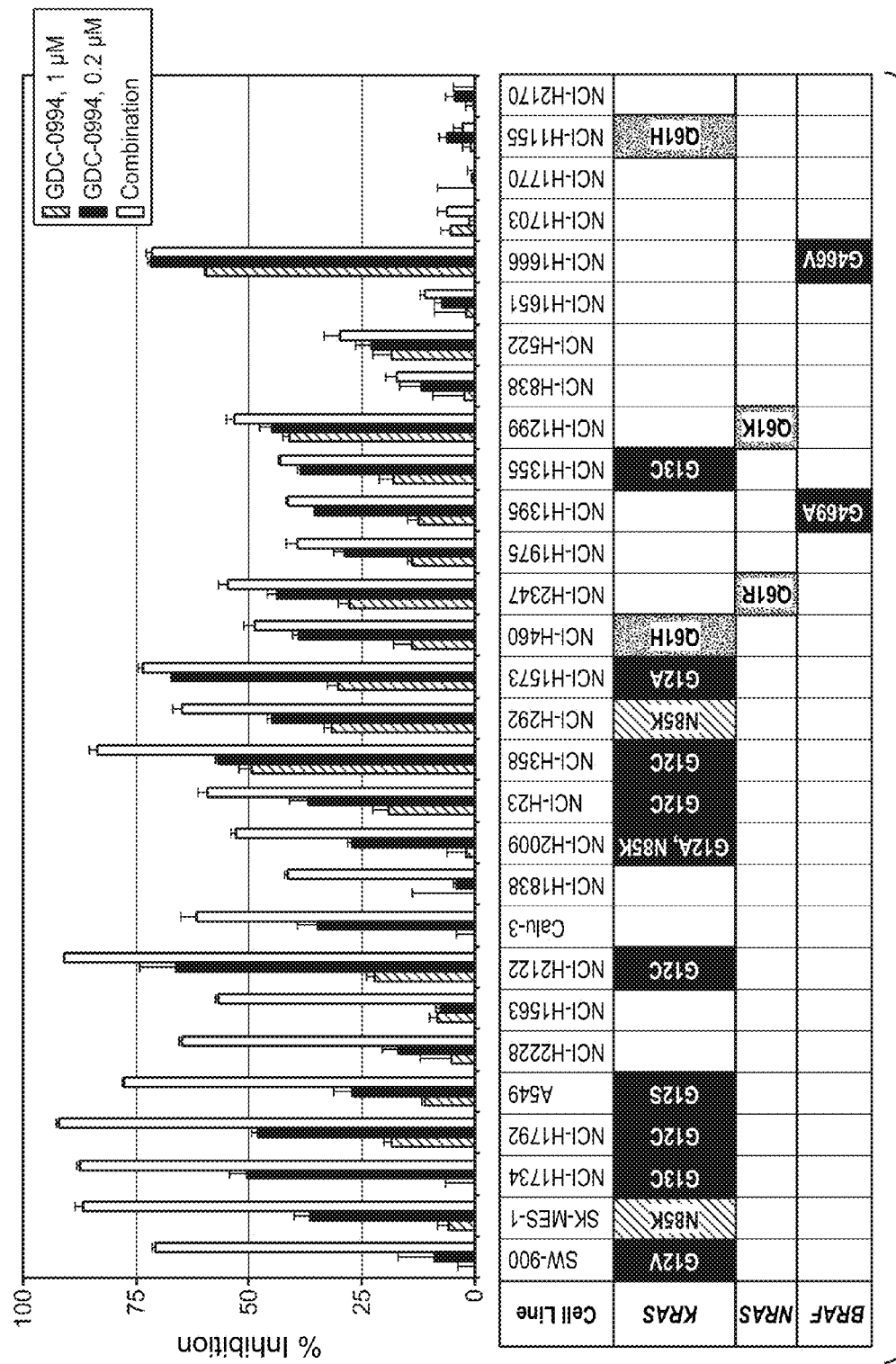

FIG. 5 shows treatment of NSCLC cells with combinations of MEKi (GDC-0973) and ERKi (GDC-0994) inhibitors. 19/29 cell lines tested show some combination effect with ERK+MEK. All the non-Q61H Kras mutant lines show some sensitivity to the combination. No combination effects were observed in the two Braf mutant lines in the panel.

Figure 6A:
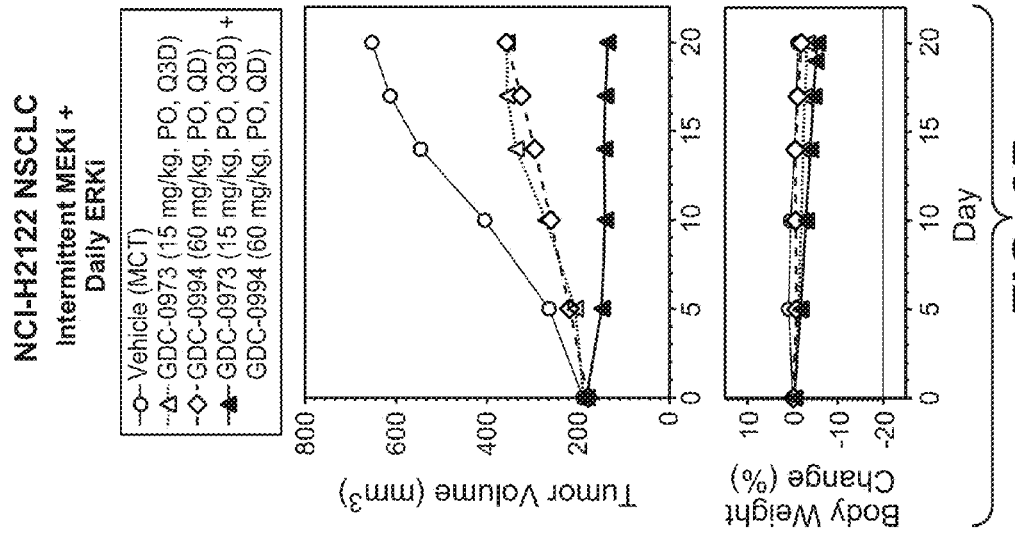
Figure 6B:
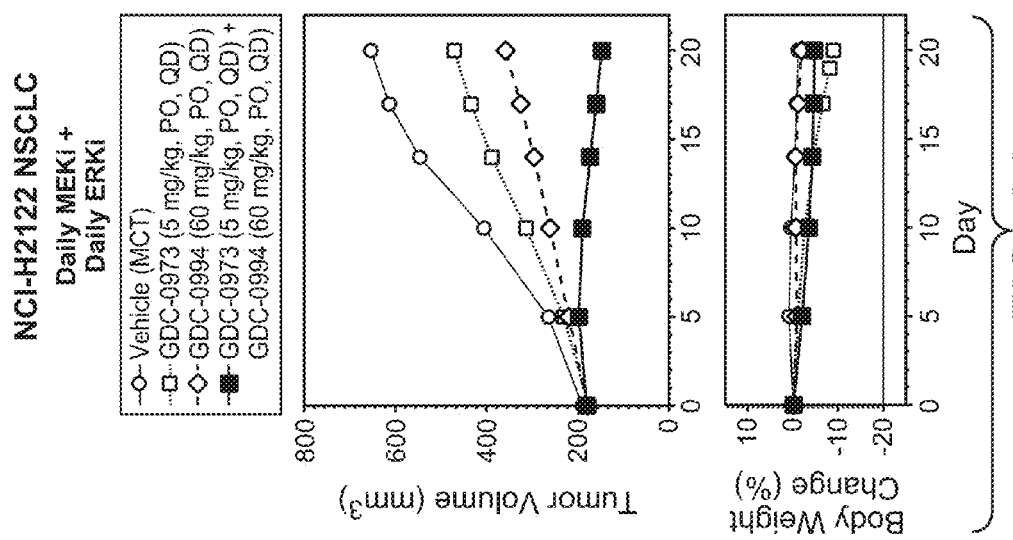
Figure 6C:
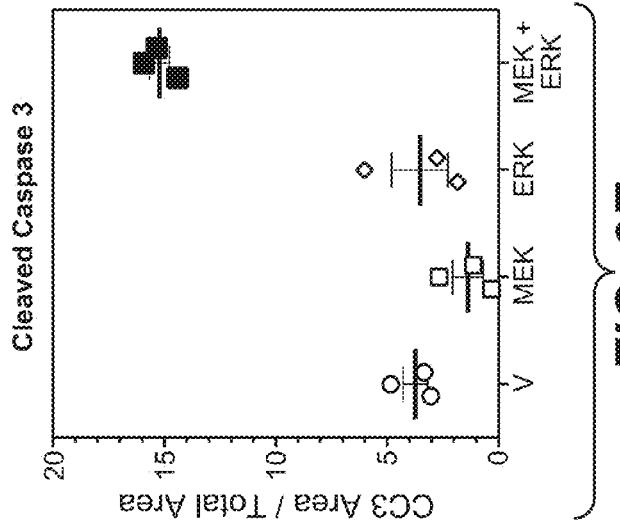
Figure 6D:
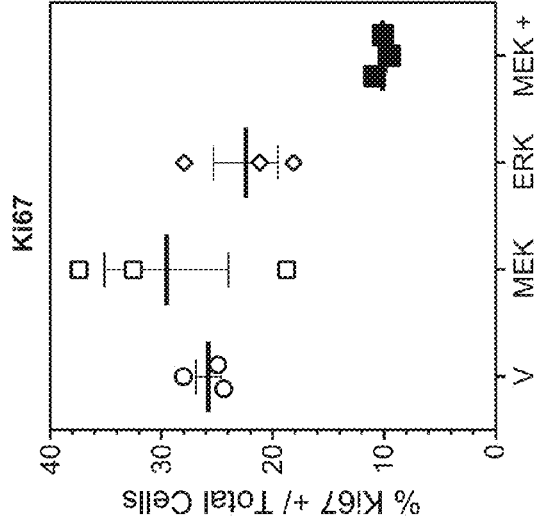
Figure 6E:
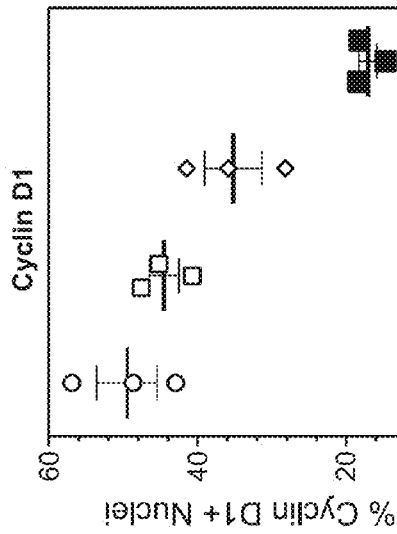

FIG. 6A, FIG. 6B, FIG. 6C, FIG. 6D and FIG. 6E show the plot of mean tumor volume change over time in Taconic female nu/nu (nude) mice with NCI-H2122 non-small cell lung cancer (NSCLC) tumor xenografts dosed daily with: MCT Vehicle (0.5% methylcellulose/0.2% Tween 80), 60 mg/kg Formula Ia (GDC-0994) and 5 mg/kg Formula II (GDC-0973) (FIG. 6A) or dosed daily with 60 mg/kg Formula Ia (GDC-0994) and 15 mg/kg every three days (Q3D, i.e., intermittent dosing) with Formula II (GDC-0973) (FIG. 6B). Mice were dosed by oral gavage. Pharmadynamic markers substantiate decreased cell growth (FIG. 6C and FIG. 6D) as evidenced by decrease in cyclic D1 and Ki67 levels and elevated apopotosis (FIG. 6E) evidenced by increase in cleaved caspase 3 in H2122 KRAS NSCLC xenograph assay6

Figures 7A, 7B, 7C:
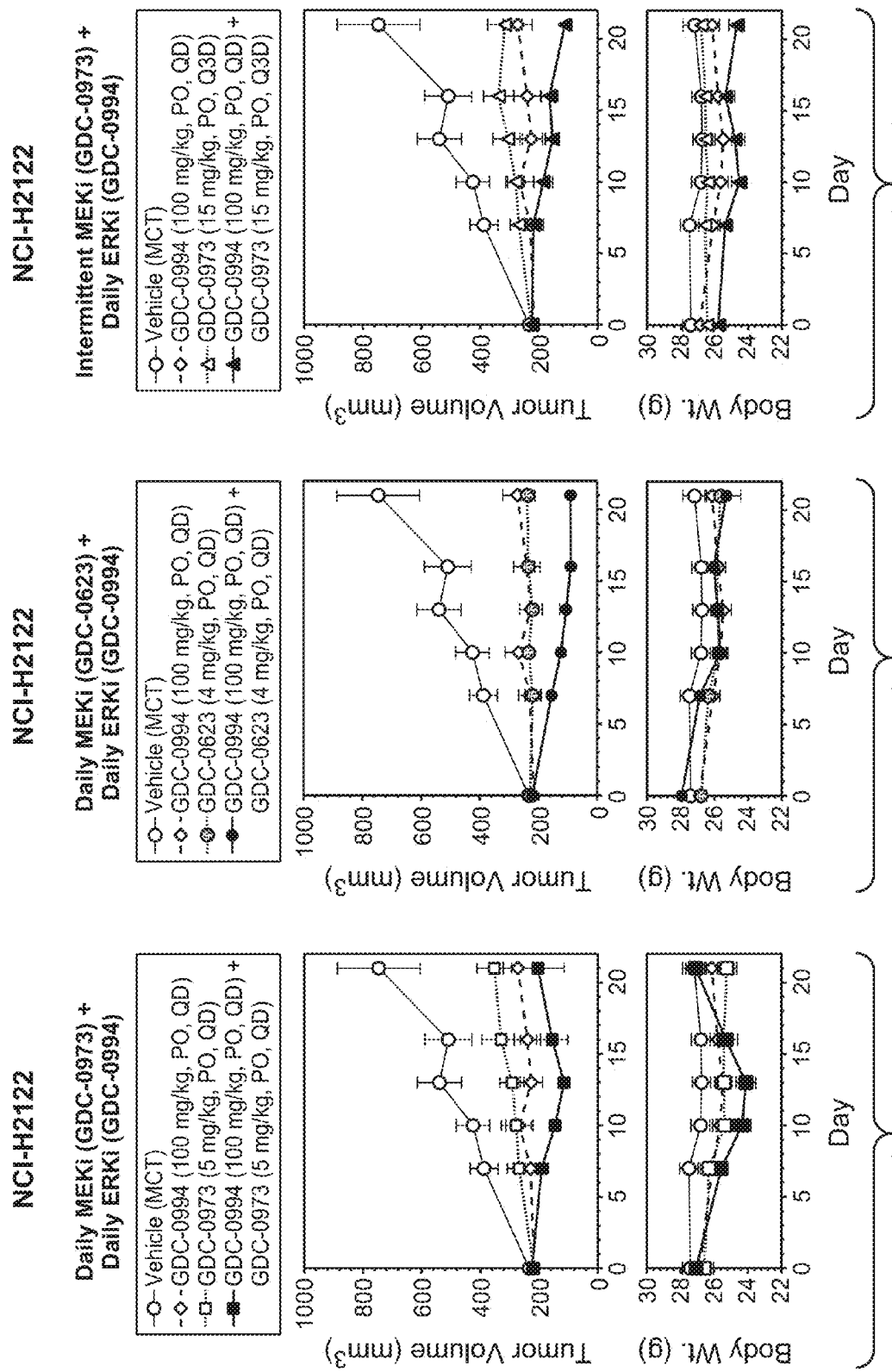

FIG. 7A, FIG. 7B and FIG. 7C show the plot of mean tumor volume change over time in Taconic female nu/nu (nude) mice with NCI-H2122 non-small cell lung cancer (NSCLC) tumor xenografts dosed daily with: MCT Vehicle (0.5% methylcellulose/0.2% Tween 80), 100 mg/kg GDC-0994 and 5 mg/kg GDC-0973 (FIG. 7A), dosed daily 100 mg/kg GDC-0994 and 4 mg/kg GDC-0973 (FIG. 7B), or dosed daily with 100 mg/kg GDC-0994 and 15 mg/kg every three days (Q3D, i.e., intermittent dosing) with GDC-0973 (FIG. 7C). Mice were dosed by oral gavage.

Figure 8A:
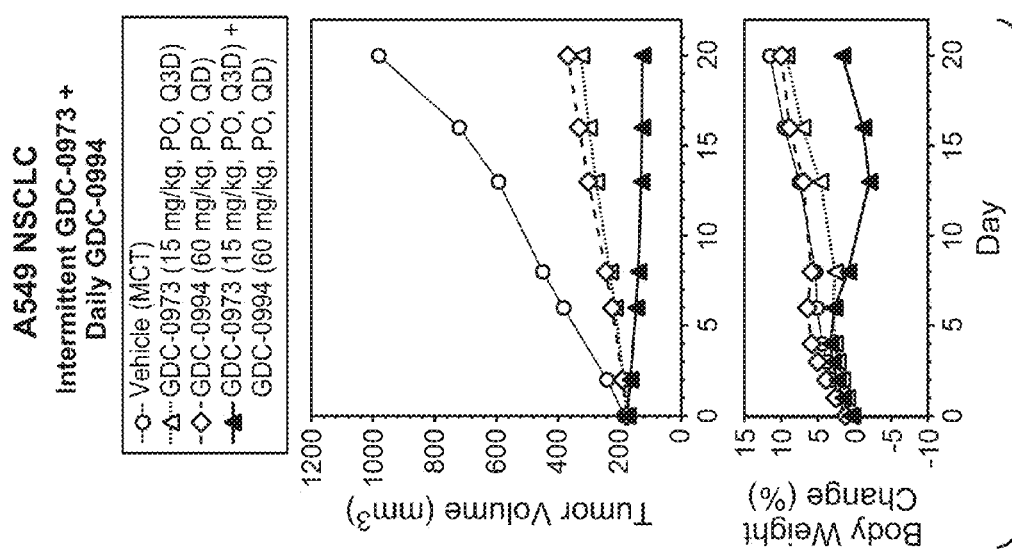
Figure 8B:
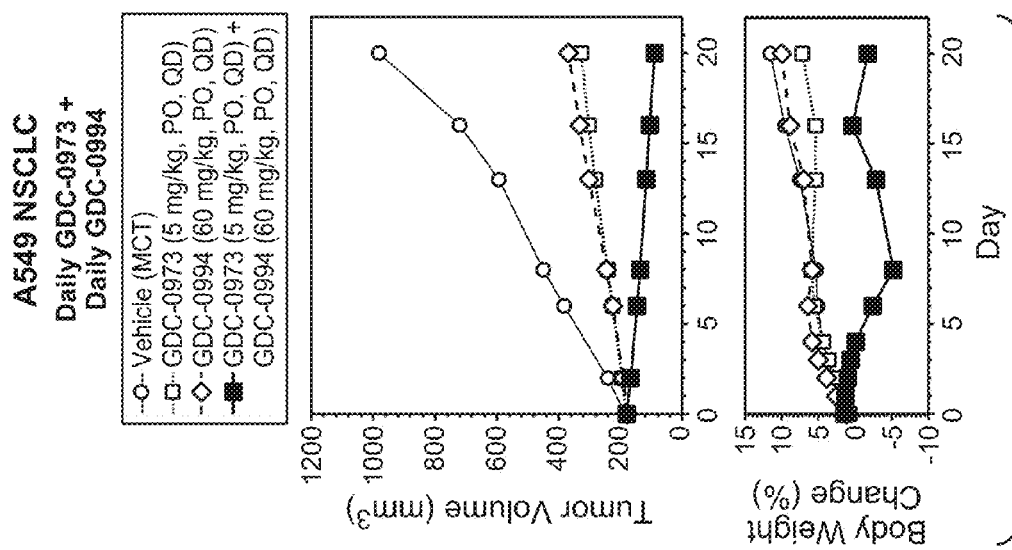

FIG. 8A and FIG. 8B show the plot of mean tumor volume change over time in Taconic female nu/nu (nude) mice with A549 non-small cell lung cancer (NSCLC) tumor xenografts dosed daily with: MCT Vehicle (0.5% methylcellulose/0.2% Tween 80), 60 mg/kg Formula GDC-0994 and 5 mg/kg GDC-0973 (FIG. 8A) or dosed daily with 60 mg/kg Formula GDC-0994 and 15 mg/kg every three days (Q3D, i.e., intermittent dosing) with GDC-0973 (FIG. 8B). Mice were dosed by oral gavage.

FIG. 9 shows a summary of efficacy of GDC-0994 and GDC-0973 in HCT 116 colorectal cancer cell line dose ranging combination efficacy study expressed as per tumor growth inhibition. Cells in grey indicate the best efficacy for a tolerated regimen. Cells in black were not tolerated. Dosing was daily (QD) oral gavage (PO).

Figure 10B:
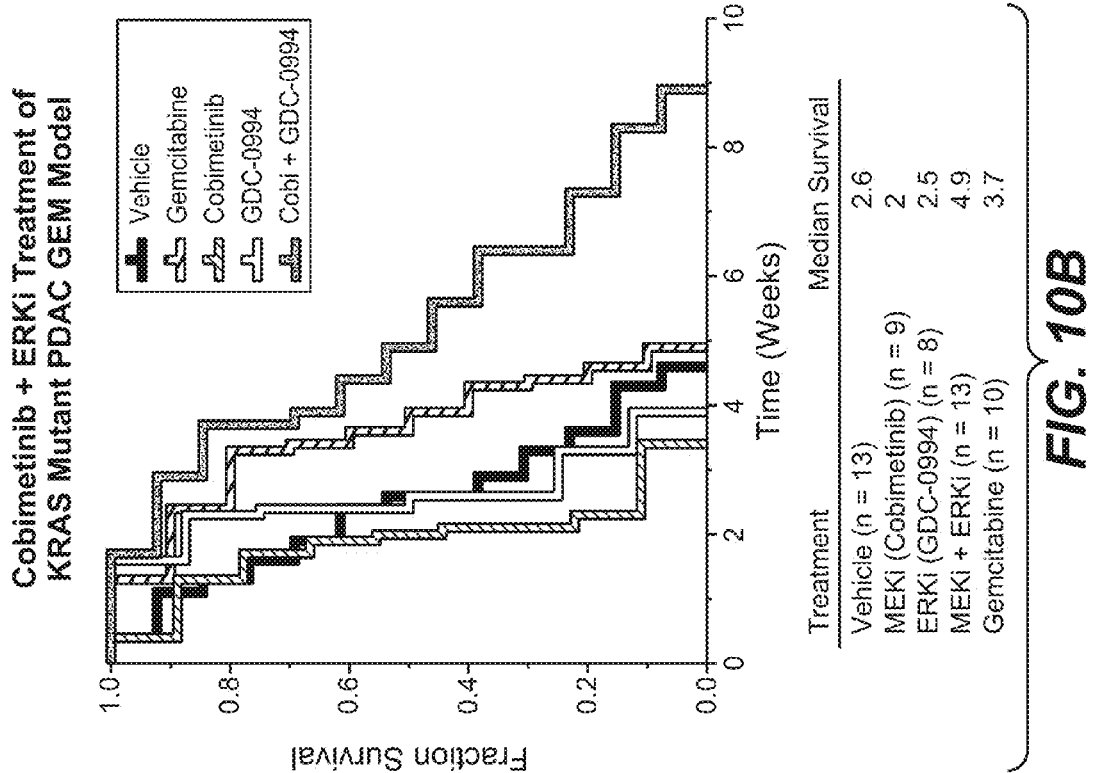
Figure 10A:
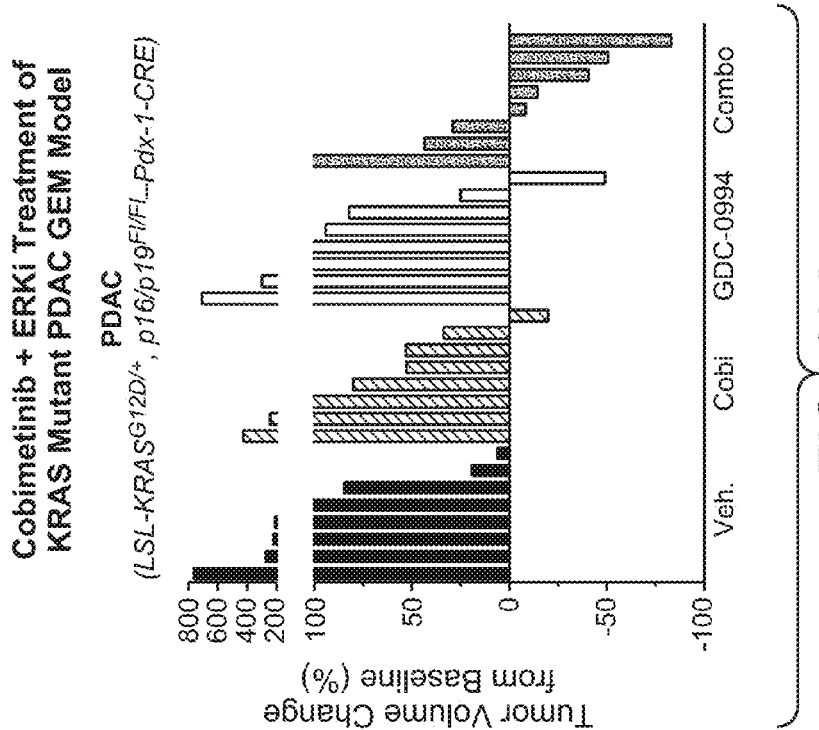

FIG. 10A and FIG. 10B depict robust anti-tumor activity of cobimetinib and GDC-0994 in KRAS mutant GEM models of pancreatic ductal adenocarcinoma (PDAC) Tumor-bearing Kras mutant GEM models were treated with vehicle, GDC-0973 (5 mg/kg, PO, QD), GDC-0994 (60 mg/kg, PO, QD) or combination of GDC-0973 and GDC-0994. FIG. 10A displays Waterfall plots depicting percent tumor volume change from baseline based on ultrasound imaging (day 0, day 7) in PDAC model following 7 day treatment with vehicle (black, n=8), cobimetinib (green, n=8), GDC-0994 (blue, n=8) and combination (red, n=9) FIG. 10B Kaplan-Meier plot of overall survival from PDAC model from treatment cohorts Vehicle (black, n=13), gemcitabine (orange, n=10), IIb (green, n=9), GDC-0994 (blue, n=8) and combination of GDC-0994 and GDC-0973 (red, n=13). Combination treatment is significant relative to Vehicle, **p<0.0001 and gemcitabine, *p=0.0159, log-rank.

Figure 11A:
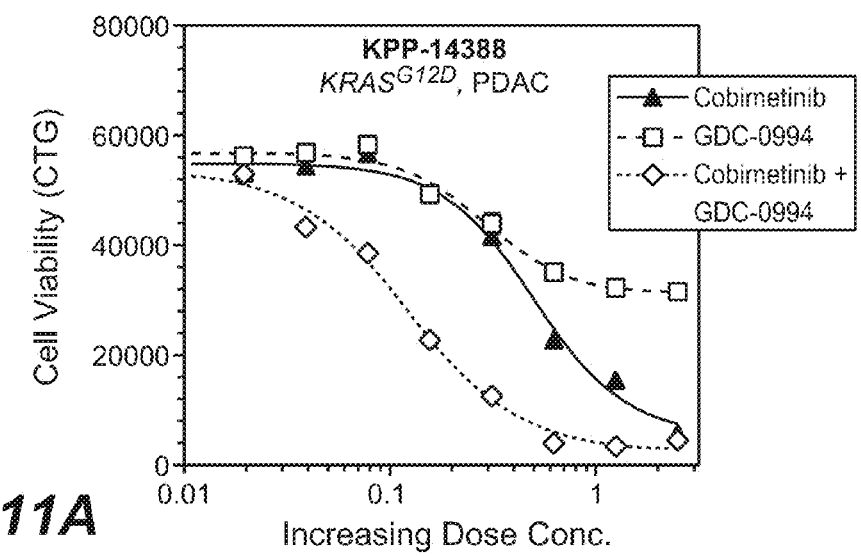
Figure 11B:
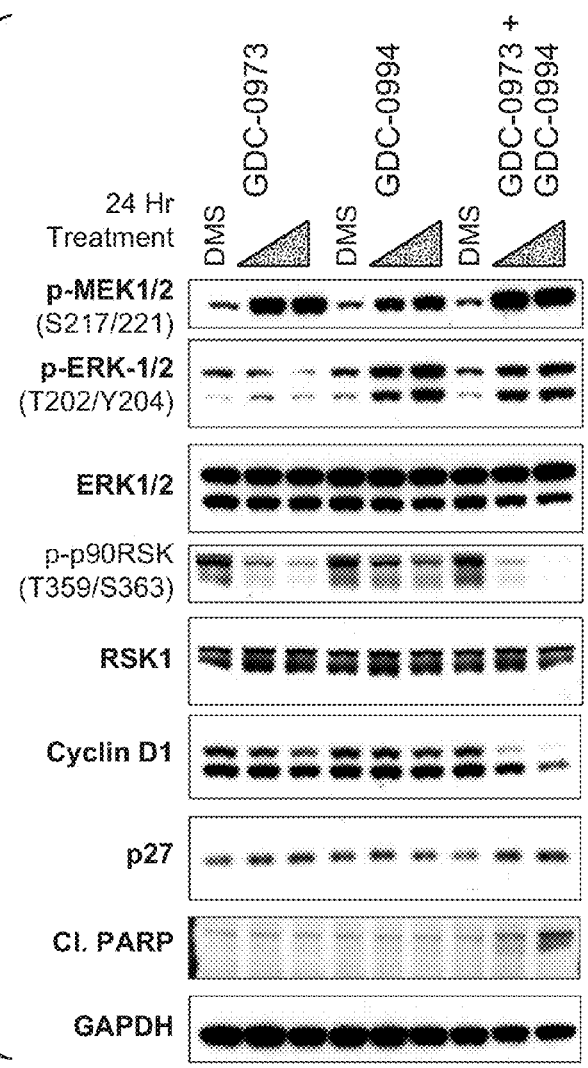

FIG. 11A and FIG. 11B. FIG. 11A show viability of $KRAS^{G12D}$, $p16/19^{FL/FL}$ PDX-CRE-derived cell lines in the presence of GDC-0973, GDC-0994 and combinations of GDC-0994 and GDC-0973 due to increased MAPK pathway suppression. FIG. 11B shows PD markers in $KRAS^{G12D}$, $p16/19^{FL/FL}$PDX-CRE-derived cell lines in the presence of GDC-0973, GDC-0994 and combinations of GDC-0994 and GDC-0973.

Figure 12:
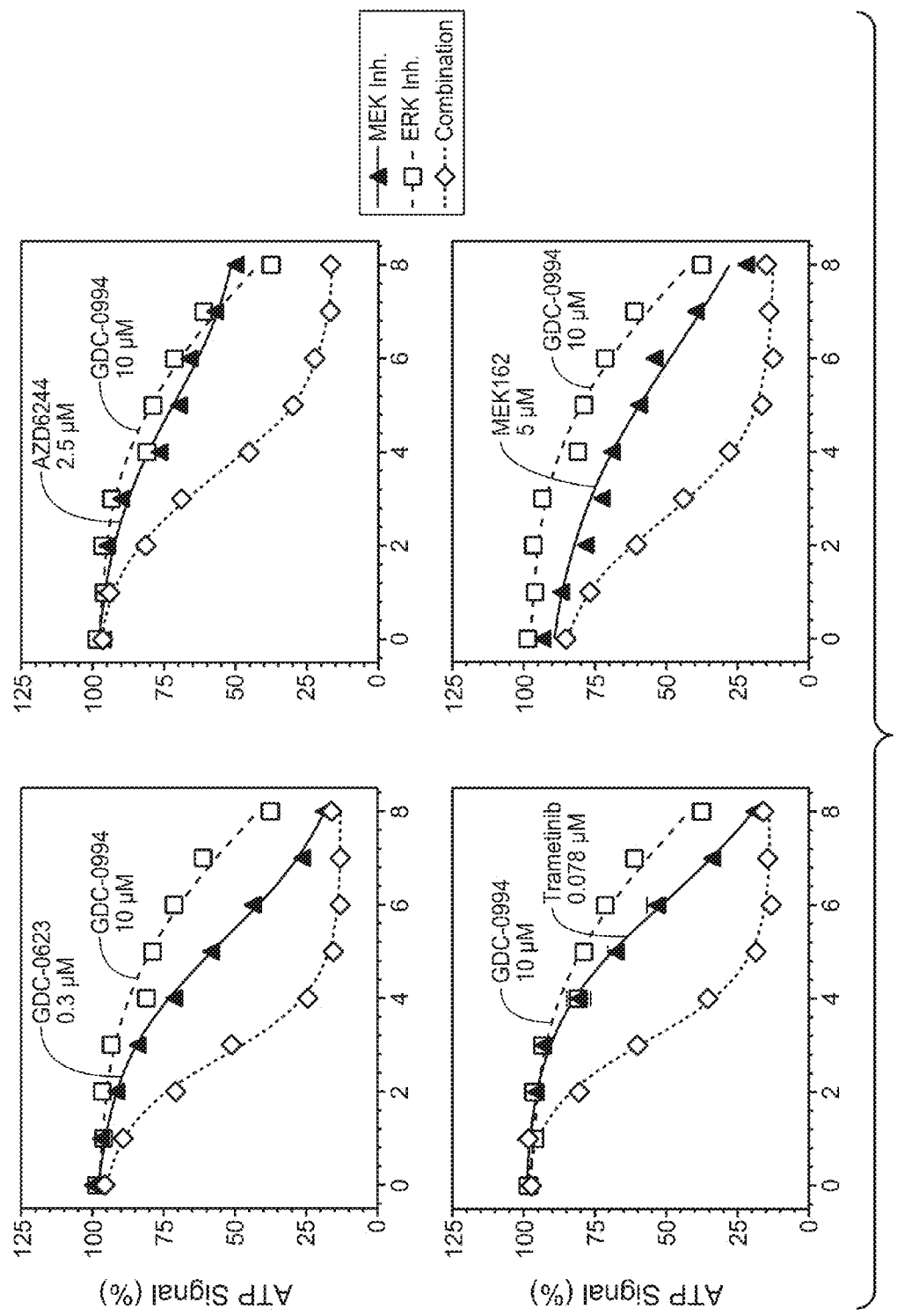

FIG. 12 shows cell growth activity observed with combinations of GDC-0994 and multiple MEK inhibitors in development.

Figure 3:
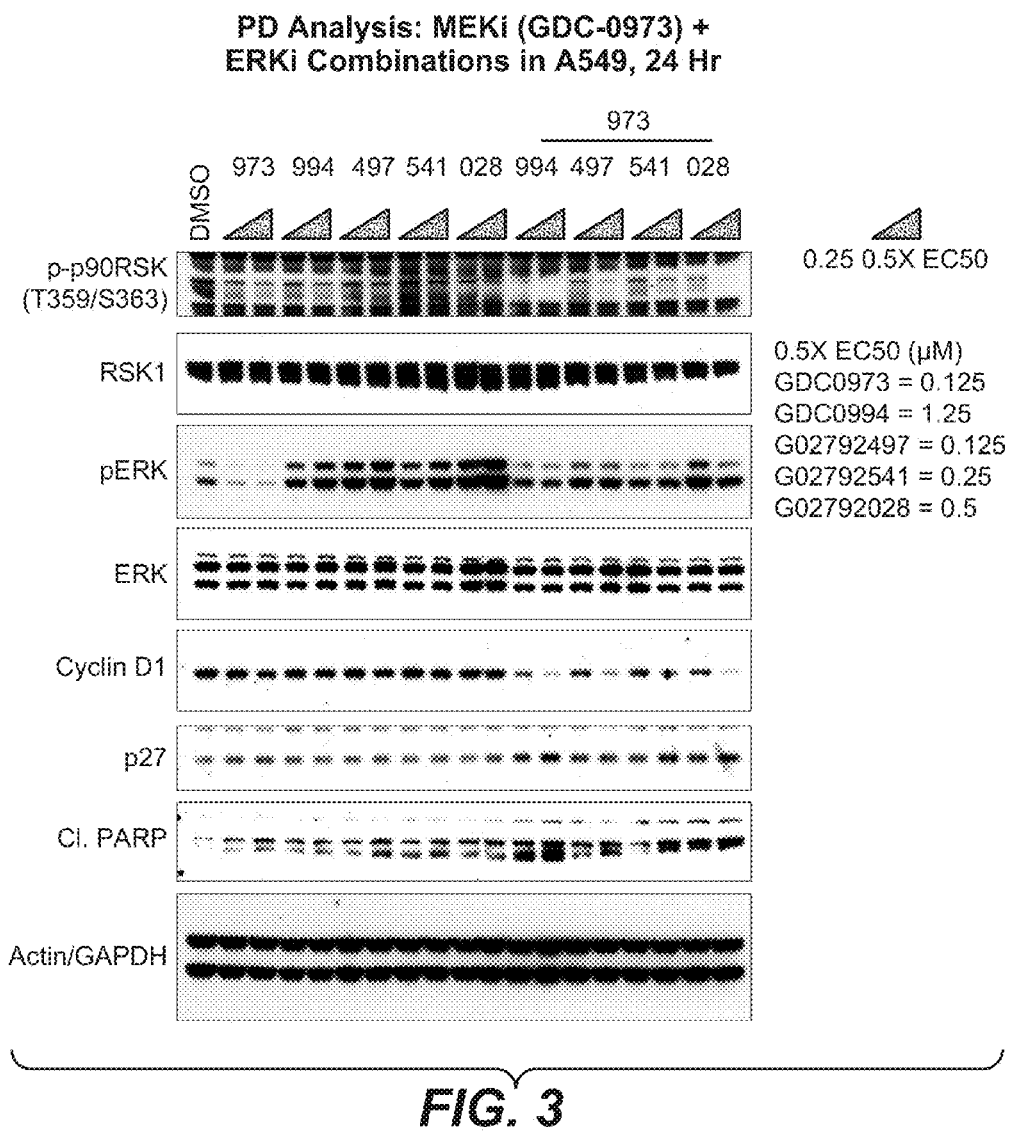
FIG. 3 shows the pharmacodynamic consequences of treatment with combination MEK and ERK inhibitors alone or in combination. Phosphorylation of RSK by ERK is inhibited. Cell cycle progression is significantly decreased as evidenced by a decrease in cyclin D1 and increase in p27. Elevated cell death (apoptosis) is evidenced by increased levels of cleaved PARP.
Figure 13A:
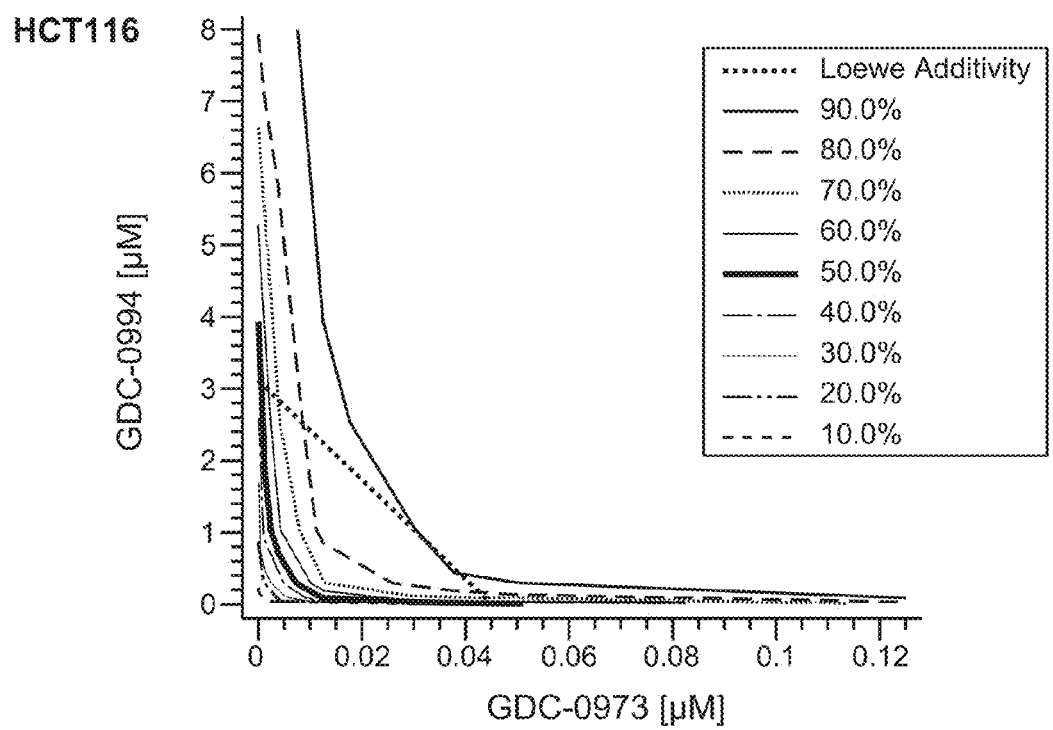
Figure 13C:
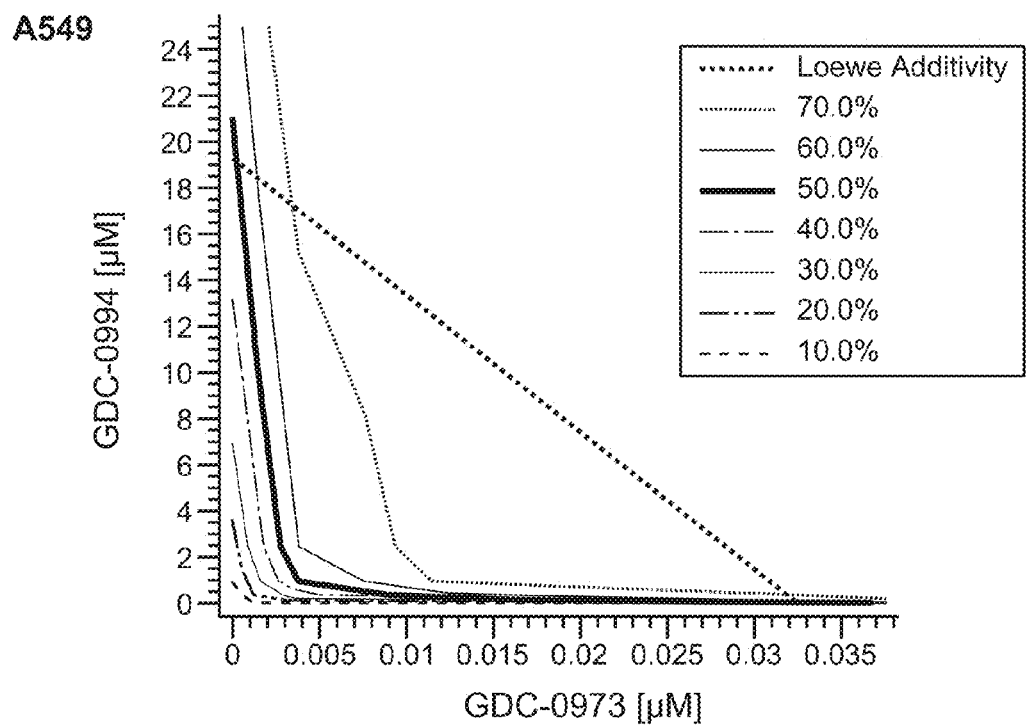
Figures 1, 13B:
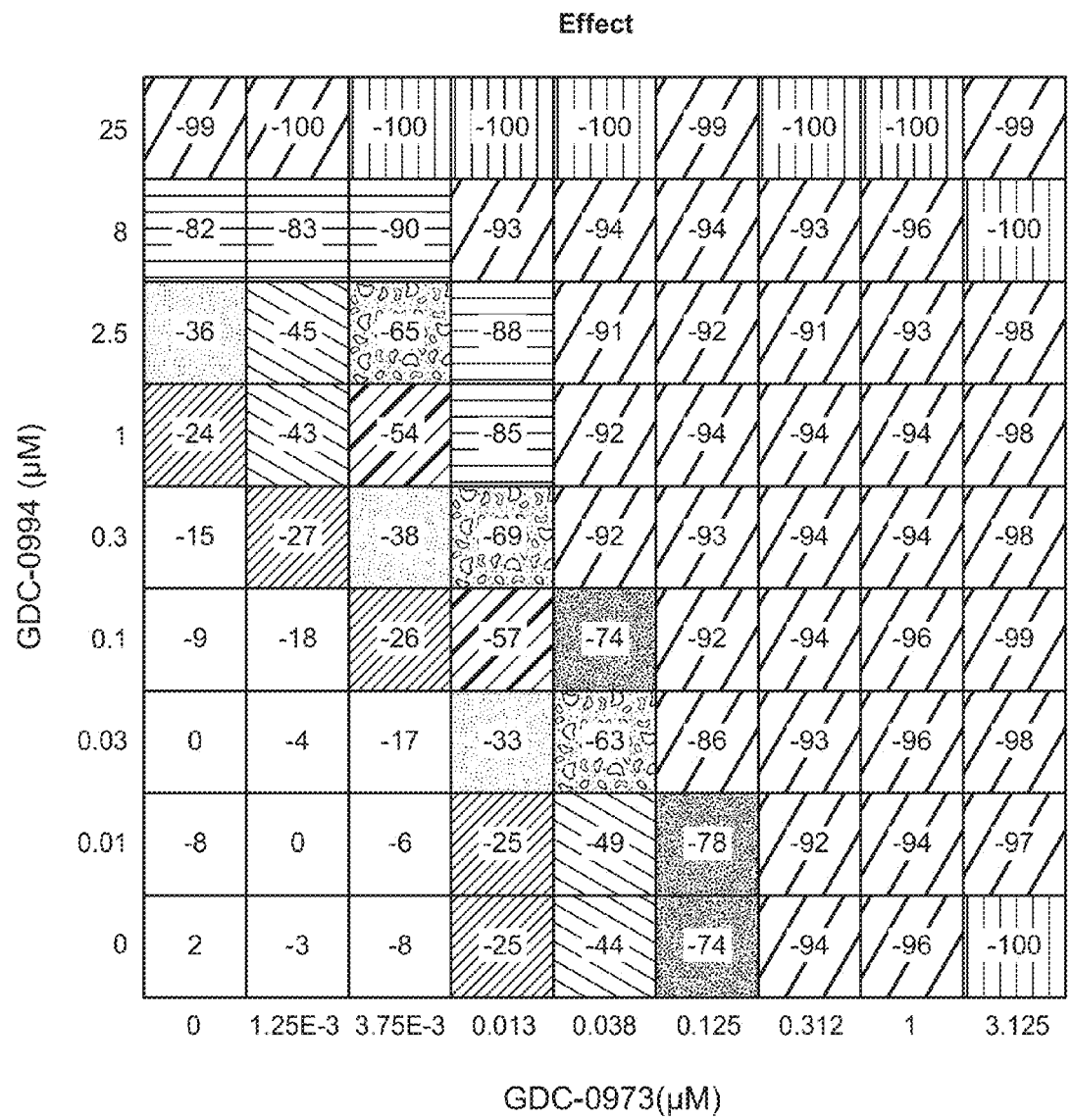
Figures 2, 13B:
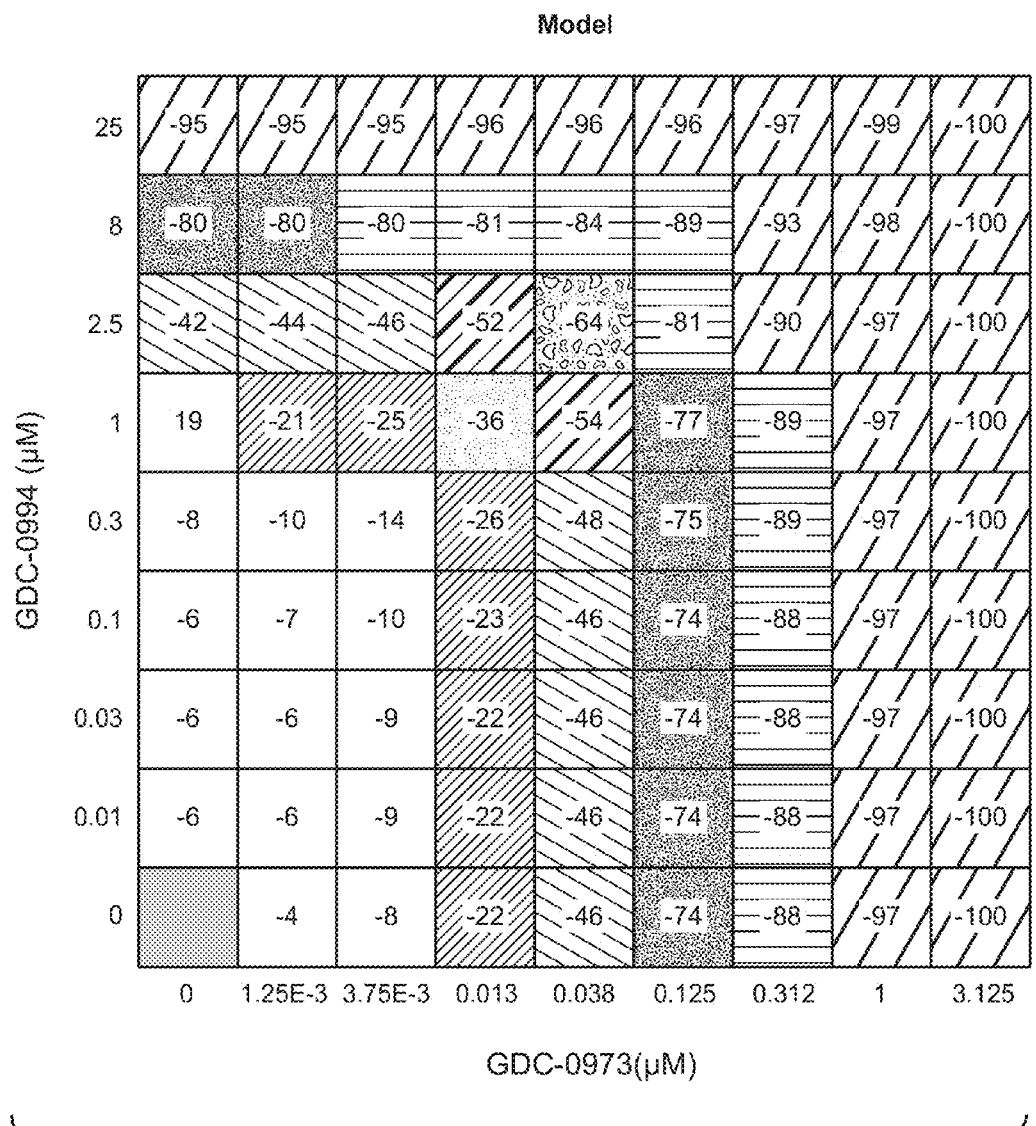
Figures 3, 13B:
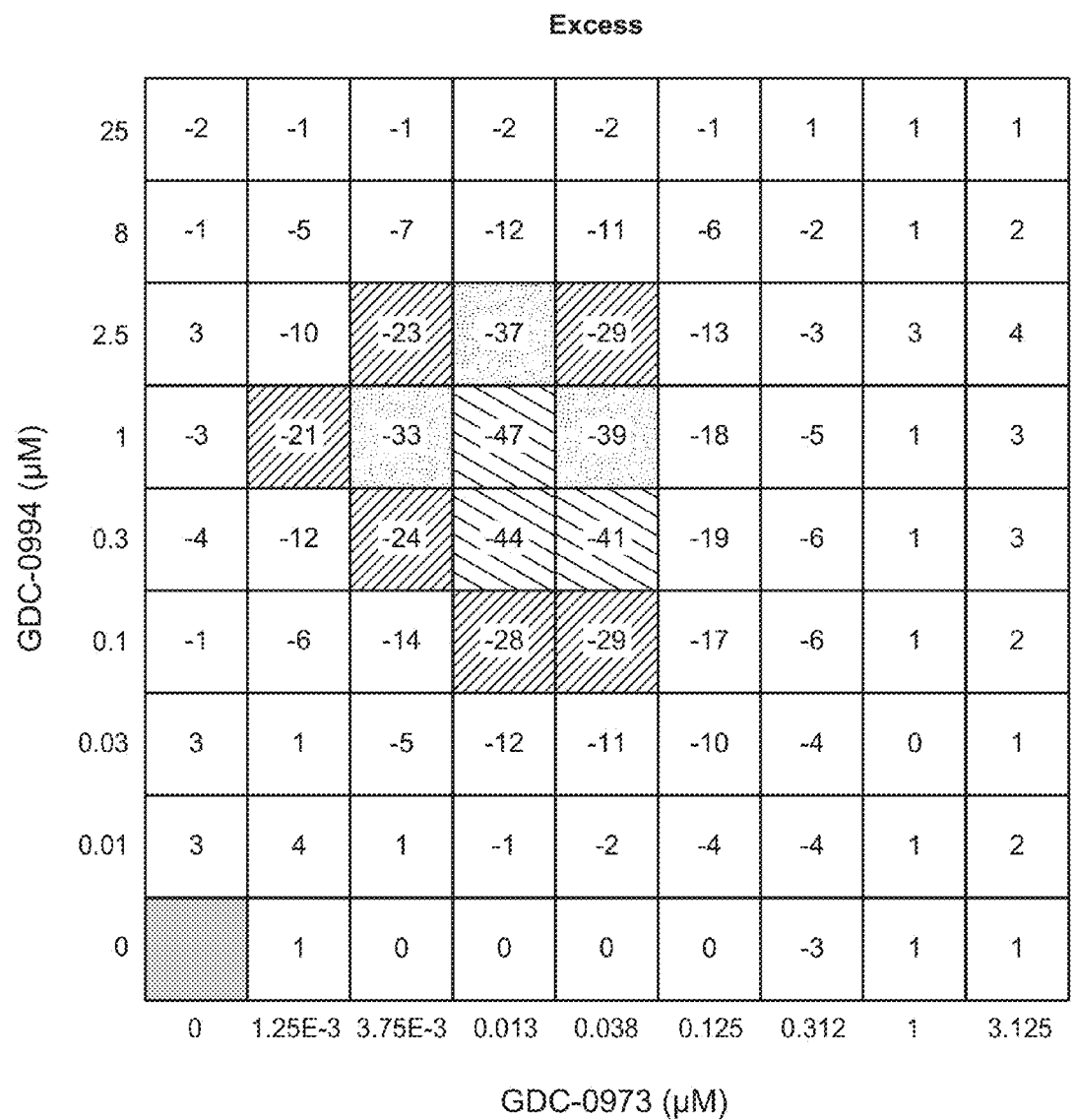
Figures 1, 13D:
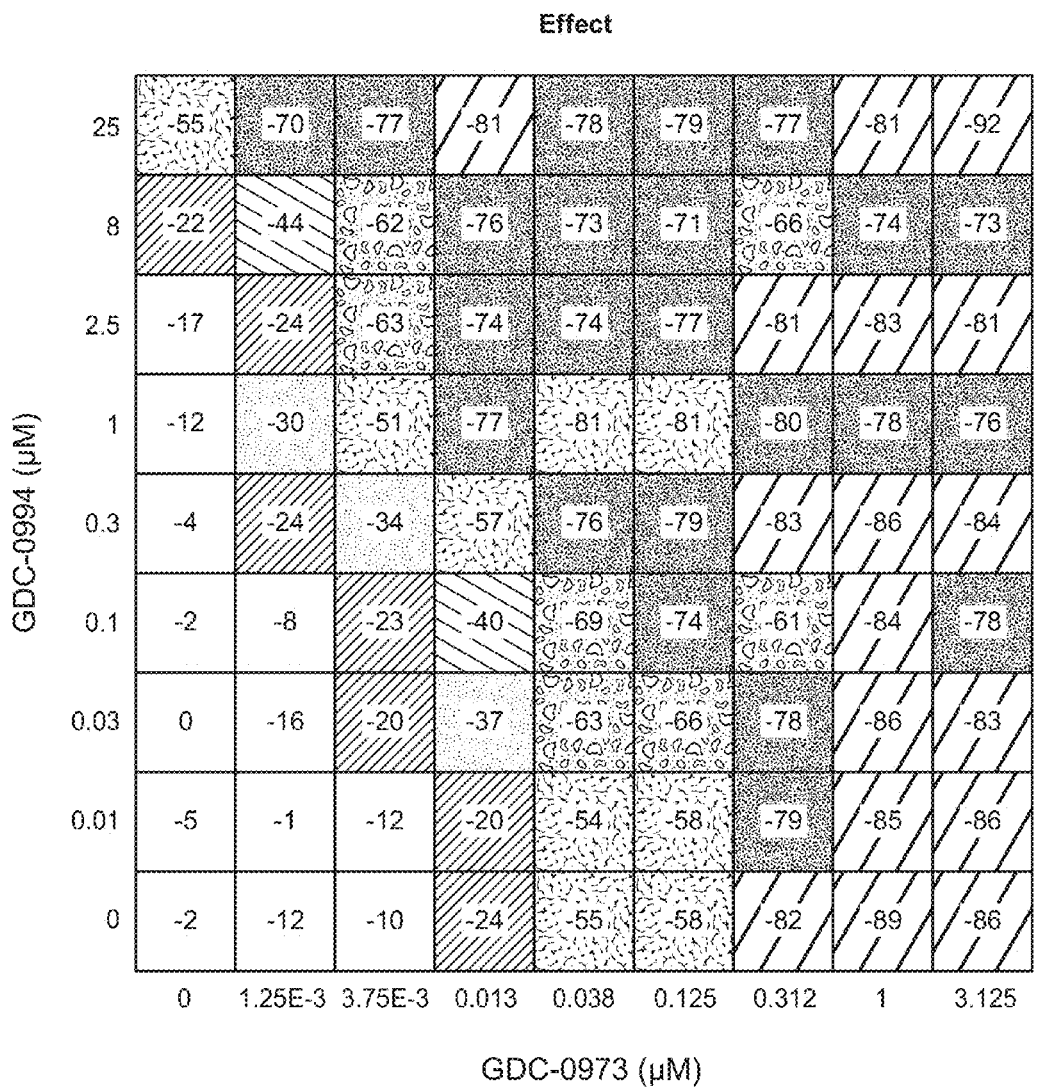
Figures 2, 13D:
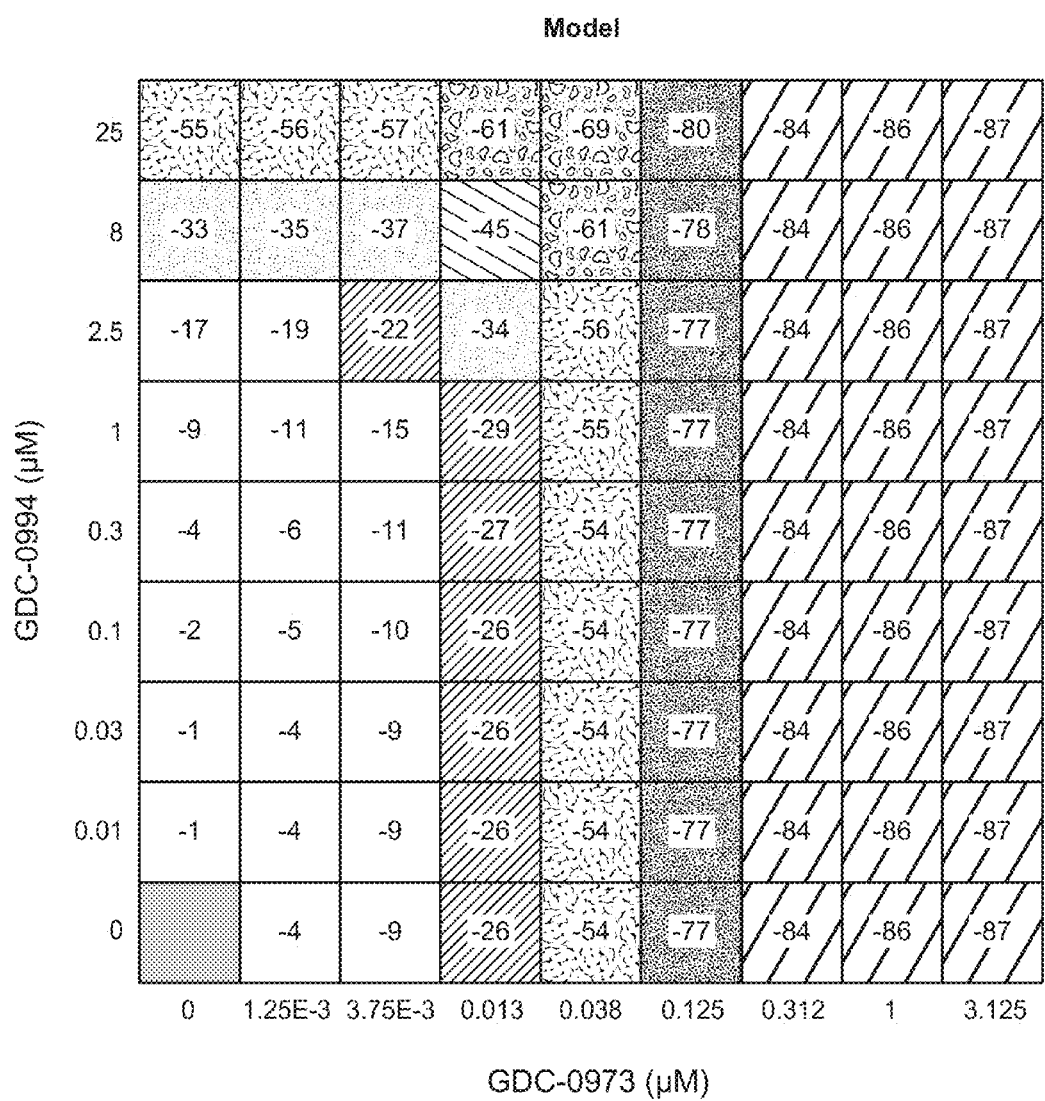
Figures 3, 13D:
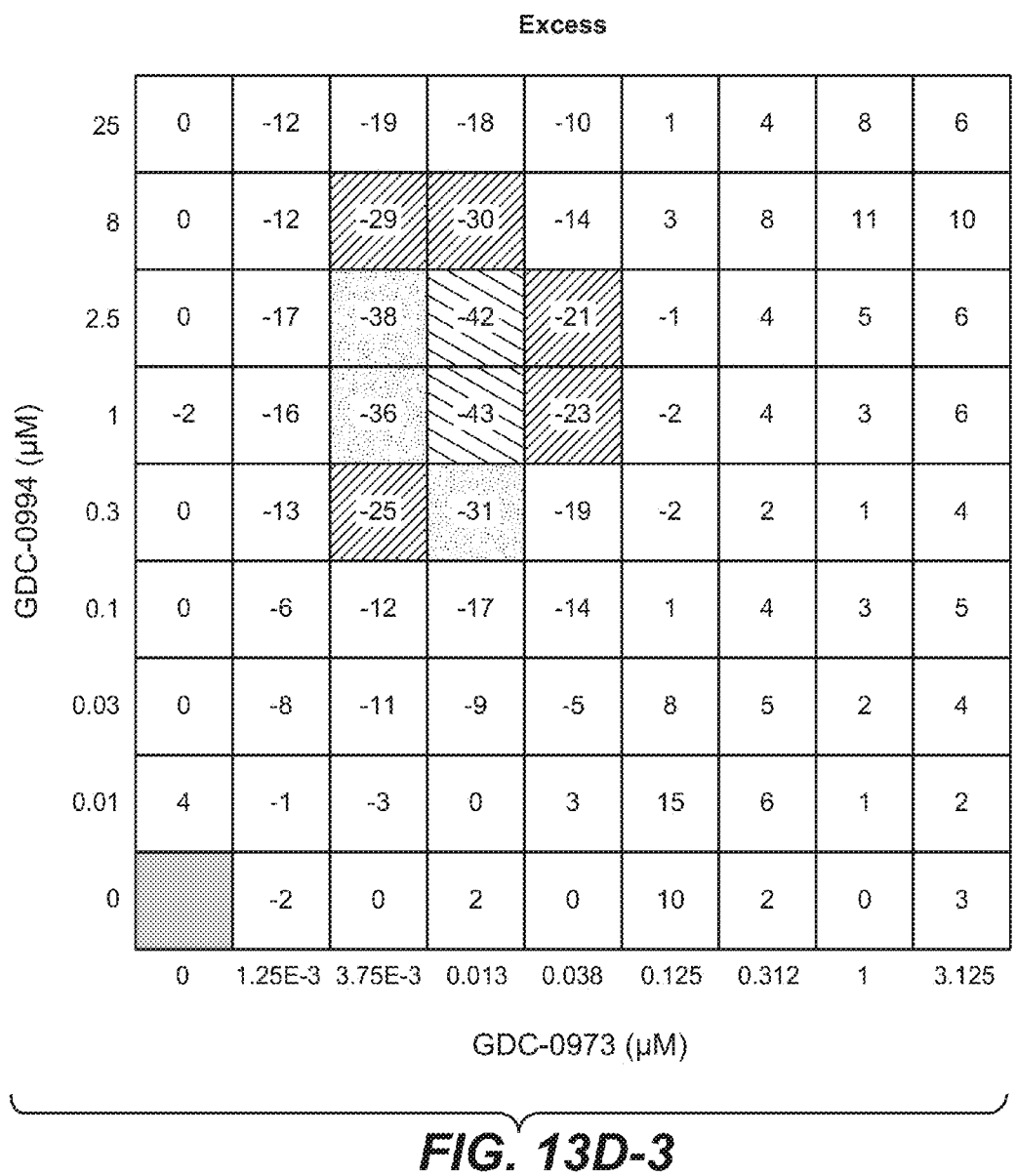

FIG. 13A, FIG. 13C, FIG. 13B-1, FIG. 13B-2, FIG. 13B-3, FIG. 13-D-1, FIG. 13D-2 and FIG. 13D-3 depict evaluation of synergistic inhibition of DNA synthesis. Exponentially growing HCT116 (A, B) and A549 (C, D) cells were treated with the indicated concentrations of GDC-0994 and GDC-0973 for 47 hours prior to addition of 5-ethynyl-2'-deoxyuridine (EdU) for 60 minutes, followed by paraformaldehyde fixation and labeling of EdU-containing DNA with Alexa Fluor 647 azide (Life Technologies, Madison Wis.). Total number of Hoechst 33542-labelled nuclei and fraction of EdU-labeled nuclei were determined by automated fluorescence microscopy and image analysis using Perkin Elmer Opera instrument and Acapella software.

FIG. 13 A and FIG. 13C show isobologram plots. Lines join points of equal inhibition of DNA synthesis attained by different combinations of the two drugs. Heavy dashed diagonal line shows the expected 50% inhibition isobole if compound combinations showed simple additivity according to the Loewe model (N. Geary, Understanding synergy. *Am. J. Physiol. Endocrinol. Metab.* 2012. doi:10.1152/ajpendo.00308.2012).

FIG. 13B-1, FIG. 13B-2, FIG. 13B-3, FIG. 13-D-1, FIG. 13D-2 and FIG. 13D-3 show dose matrix synergy analysis showing 1; Observed percent change in fraction of EdU-positive cells relative to DMSO-treated controls, 2; Predicted effect of drug combinations based on the Loewe additivity model applied to the single-agent dose-response curves, 3; difference between observed data and predicted additive effects. Numbers less than zero indicated greater inhibition of DNA synthesis than expected for additive drugs.

Data was analyzed using the Compound Synergy Extension module of Genedata Screener (Genedata AG, Basel)

DETAILED DESCRIPTION OF THE INVENTION

Definitions

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to therapeutic treatment, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder, e.g., a patient with cancer.

To "inhibit" is to decrease or reduce an activity, function, and/or amount as compared to a reference.

The phrase "therapeutically effective amount" means an amount that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount may reduce the number of cancer cells; reduce the tumor size; inhibit (e.g., slow to some extent and preferably stop) cancer cell infiltration into peripheral organs; inhibit (e.g., slow to some extent and preferably stop) tumor metastasis; inhibit, to some extent, tumor growth; and/or relieve to some extent one or more of the symptoms associated with the cancer. To the extent the combination may prevent growth and/or kill existing cancer cells, it may be cytostatic and/or cytotoxic. For cancer therapy, efficacy can be measured, for example, by assessing the time to disease progression (TTP) and/or determining the response rate (RR).

In addition to providing improved treatment for a given hyperproliferative disorder, administration of certain combinations of the invention may improve the quality of life for a patient compared to the quality of life experienced by the same patient receiving a different treatment. For example, administration of a combination to a patient may provide an improved quality of life compared to the quality of life the same patient would experience if they received only one of the individual agents as therapy. For example, the combined therapy with a combination described herein may lower the dose of therapeutic agents needed. The combination therapy may also decrease or eliminate the need for the use of chemotherapeutic agents and the side-effects associated with high-dose chemotherapeutic agents (e.g. nausea, vomiting, hair loss, rash, decreased appetite, weight loss, etc.). The combination may also cause reduced tumor burden and the associated adverse events, such as pain, organ dysfunction, weight loss, etc. Accordingly, one aspect of the invention provides a combination for therapeutic use for improving the quality of life of a patient treated for a hyperproliferative disorder with an agent described herein.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver.

The term "mammal" includes, but is not limited to, humans, mice, rats, guinea pigs, monkeys, dogs, cats, horses, cows, pigs, sheep, and poultry. The term patient refers to a mammal, and in one embodiment, the patient is a human male or a human female.

The term "synergistic" as used herein refers to a therapeutic combination which is more effective than the additive effects of the two or more single agents. A determination of a synergistic interaction may be based on the results obtained from the assays known in the art. The results of these assays can be analyzed using the Chou and Talalay combination method and Dose-Effect Analysis with CalcuSyn software in order to obtain a Combination Index (Chou and Talalay, *Adv. Enzyme Regul.* 1984 22:27-55). The combinations provided herein can be analyzed utilizing a standard program for quantifying synergism, additivism, and antagonism among anticancer agents. An example program is that described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together. Combination effects were evaluated using both the BLISS independence model and the highest single agent (HSA) model (Lehár et al. 2007, Molecular Systems Biology 3:80). BLISS scores quantify degree of potentiation from single agents and a positive BLISS score (greater than 0) suggests greater than simple additivity. A cumulative positive BLISS score greater than 250 is considered strong synergy observed within the concentration ranges tested. An HSA score (greater than 0) suggests a combination effect greater than the maximum of the single agent responses at corresponding concentrations.

Methods of measuring TGI are known in the art. In one example method, average tumor volumes are determined and compared from the patient before and after treatment. Tumor volumes can be measured in two dimensions (length and width) using any method in the art, for example UltraCal IV calipers (Fred V. Fowler Company) or by PET (positron emission tomography), or by some other method. The formula tumor volume $(mm^3)=(length \times width^2) \times 0.5$ can be used. Measuring tumor volumes over multiple time periods can be done using a mixed-modeling Linear Mixed Effects (LME) approach (Pinheiro et al. 2009). This approach can address both repeated measurements (and multiple patients). Cubic regression splines can be used to fit a non-linear profile to the time courses of tumor volume at each dose level. These non-linear profiles can then be related to dose within the mixed model. Tumor growth inhibition as a percent of vehicle can be calculated as a percent area under the fitted curve (AUC) per day in relation to the vehicle, using the following formula:

$$\% \, TGI = 100 \left[1 - \left(\frac{AUC_{treatment}/\text{day}}{AUC_{vehicle}/\text{day}}\right)\right]$$

Using this formula, a TGI value of 100% indicates tumor stasis, greater than about 1% but less than about 100% indicates tumor growth inhibition, and greater than about 100% indicates tumor regression.

MEK Inhibitors

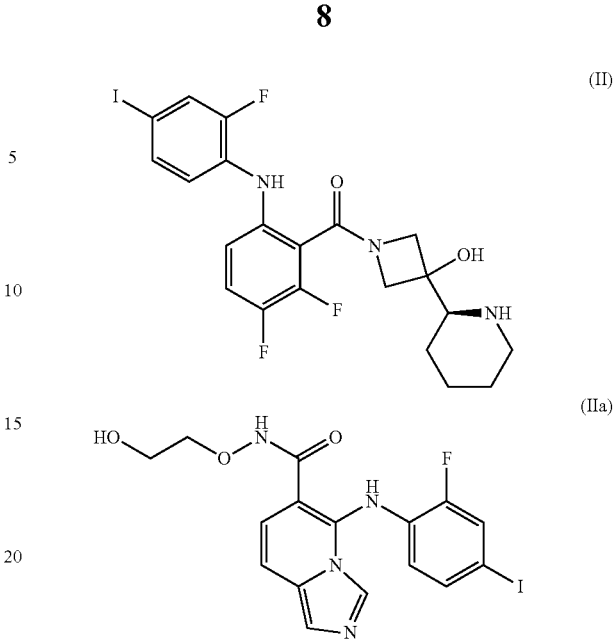

The present invention relates to MEK inhibitors and their use in a combination therapy with HER3 and EGFR inhibitors. MAK inhibitors have been extensively reviewed (S. Price, Putative Allosteric MEK1 and MEK 2 inhibitors, Expert Opin. Ther. Patents, 2008 18(6):603; J. I. Trujillo, MEK Inhibitors: a patent review 2008-2010 Expert Opin. Ther. Patents 2011 21(7):1045. Preferably the MEK inhibitor could be selected from GDC-0973 (cobimetinib), GDC-0623, AZD6244 (selumetinib), AZD8330, BAY 86-9766 (refametinib), GSK-1120212 (trametinib), ARRY-162, MSC1936369, MK162, TAK733 and PD-325901. Most preferably the MEK inhibitor is GDC-0973 (cobimetinib) or GDC-0623.

Cobimetinib (GDC-0973, also referred to as "Compound II" herein) is an orally available, potent and highly selective inhibitor of MEK1 and MEK2, central components of the RAS/RAF pathway and has single agent anti-tumor activity in multiple human cancer models. GDC-0973 has the chemical name [3,4-difluoro-2-[(2-fluoro-4-iodophenyl)amino] phenyl][3-hydroxy-3-[(2S)-2-piperidinyl]-1-azetidinyl] methanone. Cobimetinib has the following CAS Registry Number: 934660-93-2.

GDC-0623 (also referred to as compound IIa herein) is an orally available, potent and highly selective inhibitor of MEK1 and MEK2, central components of the RAS/RAF pathway and has single agent anti-tumor activity in multiple human cancer models. GDC-0623 has the chemical name 5-[(2-fluoro-4-iodophenyl)amino]-N-(2-hydroxyethoxy)-imidazo[1,5-a]pyridine-6-carboxamide and has the following CAS Registry Number 1168091-68-6.

ERK INHIBITORS

Erk inhibitors used for treating cancers and hyperproliferative diseases. Compounds Ia-Id inhibit ERK1 and ERK2 phosphorylation and have single agent anti-tumor activity in multiple human cancer models. ERK is the only known substrate for MEK1 and MEK2. Phosphorylation of ERK results in translocation to the nucleus where it phosphorylates nuclear targets and regulates various cellular processes such as proliferation, differentiation, and cell cycle progression (J. L. Yap et al., Chem. Med. Chem. 2011 6:38).

ERK inhibitors have been reviewed (K. Burkhard et al., Curr. Top. Med. Chem. 2009 9(8):678-689) Pyrazole and indazole ERK inhibitors also have been disclosed (D. Fairfax et al., WO2012094313; G. W. Shipps, Jr. et al., WO2012087772; G. W. Shipps, Jr. et al., WO2012036997 and Y. Deng et al., WO2012030685; A. M. Aronov et al., *J. Med. Chem.* 2009 52:6362-68)

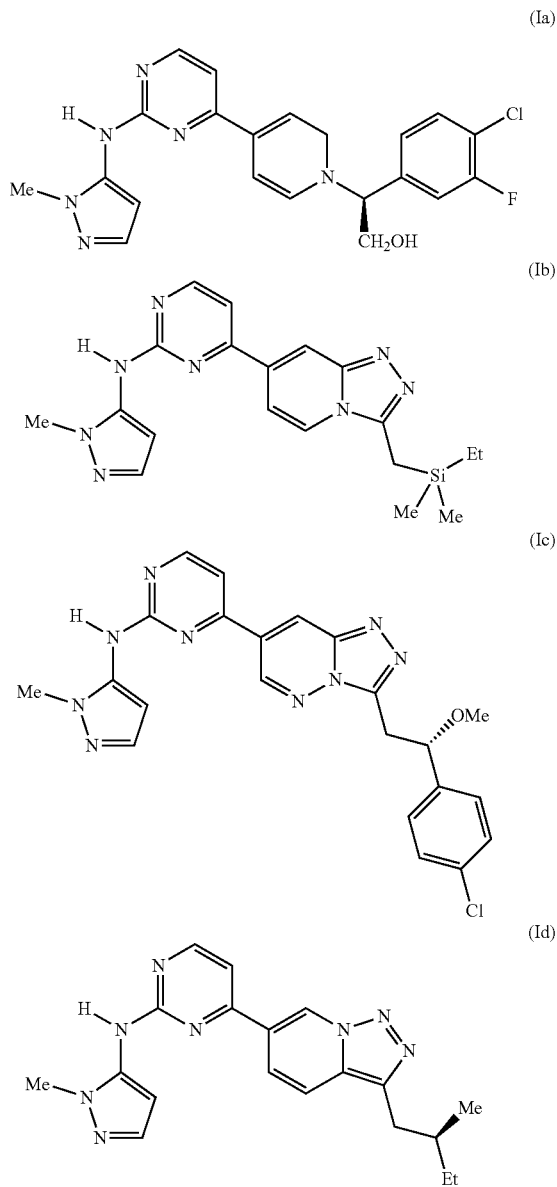

Despite recent advances in human tumor profiling and small and large molecule drug design leading to the discovery of targeted therapeutics that have altered the history of the diseases for which they were initially developed, the overall success rate of targeted agents in oncology is, however, still rather low, which may be partially explained by the heterogeneity of many cancers as well as the complex pathways in which the targets act, which involve multiple redundant pathways and cross-talk among many molecular pathways.

One way to approach this problem is to treat tumors with a combination of targeted agents, or combinations of targeted agents and chemotherapeutic agents. This are approach attempts to target multiple pathways that independently and together drive proliferation in many tumors.-and are usually activated in tumors by a number of genomic events. This approach has a dual benefit: it has the potential to increase the initial tumor response rate in tumors driven by multiple oncogenic events, as well as to decrease the rates of acquired resistance that could occur with either agent alone. This is due to the inhibition of the activating compensatory pathways, which would then prolong the activity of the combination over the activity seen by either agent alone.

Combined treatment of naïve K-ras mutant cells with MEK and ERK inhibitors inhibited the out-growth of resistant cells, whereas ERK inhibitor treatment of cells with acquired MEK inhibitor resistance effectively blocked proliferation (G Hatzivassiliou et al., *Mol. Cancer Ther.* 2012 11:1143-1154). Herein we have demonstrated that simultaneous inhibition of two kinases in the same pathway resulted in improved inhibition of cell.

Figure 4:
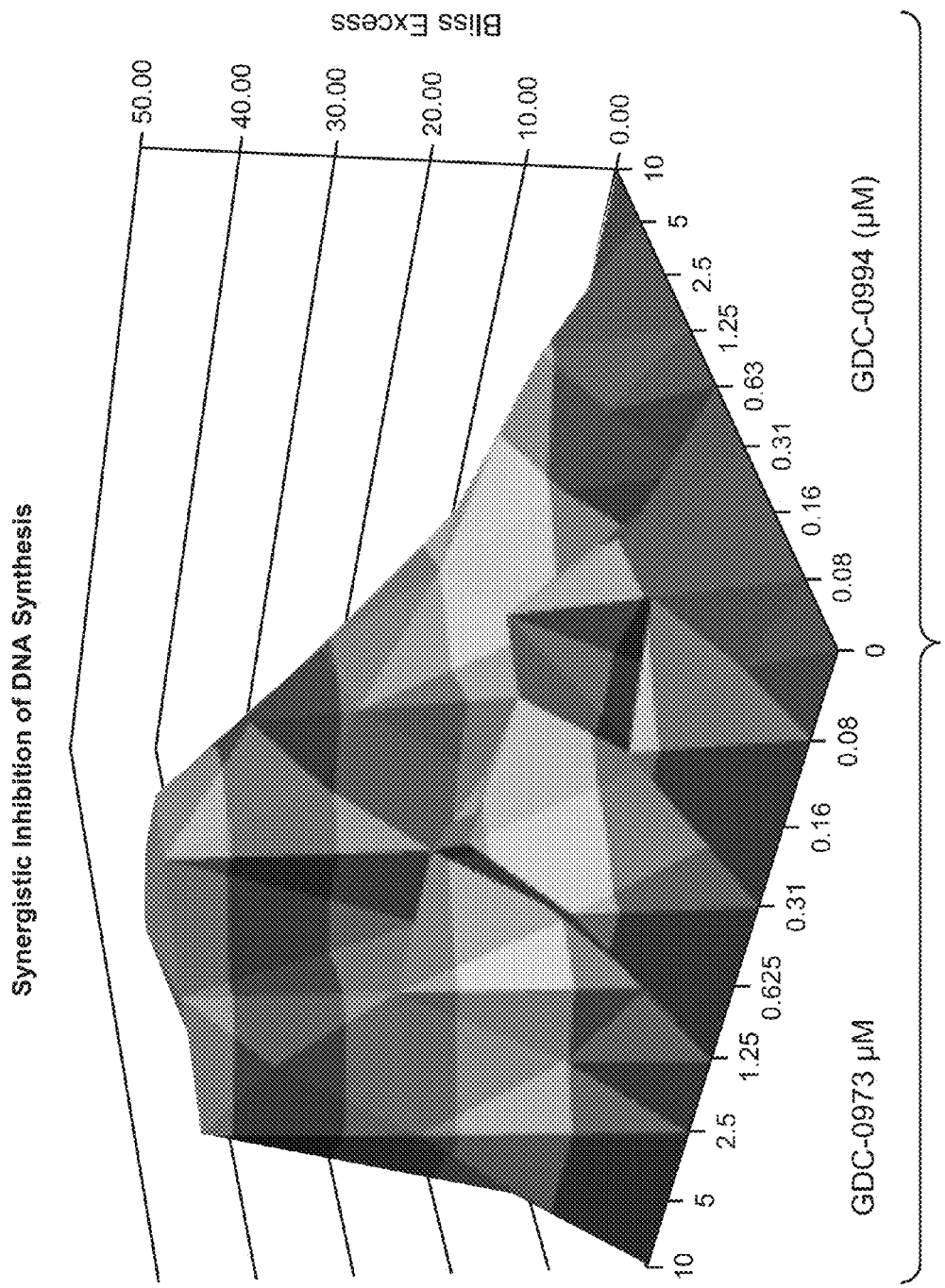
FIG. 4 shows a Bliss excess surface depicting inhibition of DNA synthesis in asynchronous exponentially-growing A549 cells determined by treating cells in 384-well plates with the indicated concentrations of each drug for 48 h. For the final 2 h of treatment cells were treated 1 uM with 5-ethynyl-2'-deoxyuridine (EdU) to label newly-synthesized DNA. Cells were then fixed and permeabilized by addition of 2% paraformaldehyde and 0.02% Triton X-100 to the growth medium for thirty minutes, followed by fluorescent labeling of incorporated EdU with Alexa-Fluor 635 azide according to the manufacturer's instructions (Life Technologies, Eugene, Oreg.) and counterstaining of DNA with Hoechst 33342.

The combination of GDC-0994 and GDC-0973 resulted in synergistic suppression of the growth A549 KRAS NSCLC cells (FIG. 5). The combination of the MEKi and ERKi resulted in attenuation of the cell cycle (decreased cyclin D1 and increased in p27 levels) and an increase in apoptosis (Increased cleaved PARP and nucELISA assays) (FIGS. 2 and 3). Coadministration of the two agents resulted in synergistic resulted in a synergist reduction in cell proliferation as measured by decreased DNA synthesis (FIG. 4). The inhibitory was also observed in vivo in xenographs with H2122 NSCLC (which also showed significant decrease in cell proliferation and increase apoptosis (FIG. 6c-6e) and A549 NSCLC cells (FIGS. 6a and 6b and 7a, 7b and 7c). Synergy was also demonstrated in GEMM model with-KRAS mutant pancreatic ductal adenocarcinoma (FIGS. 10a and 10b) wherein the same pharacodynamic markers were evident (FIGS. 11a and 11b).

Figure 1:
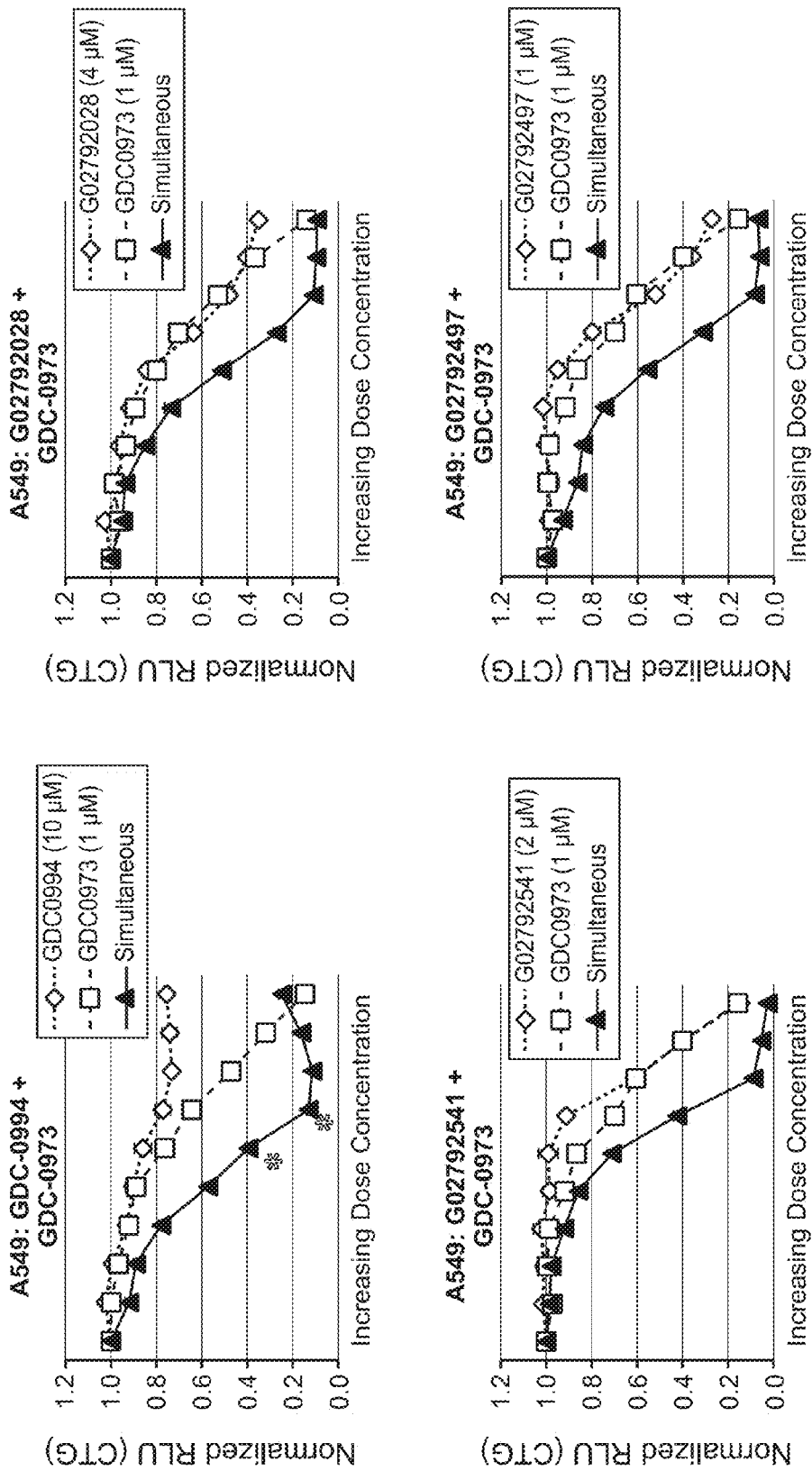
FIG. 1 shows cell proliferation of A549 non-small cell lung cancer (NSCLC) cells when dosed with GDC-0994, Ib, Ic or Id and GDC-0973 individually or dosed with GDC-0994, Ib, Ic or Id combined with GDC-0973 using the protocol in Example 6. Cells were incubated with the indicated maximal drug concentration with a 3-fold dilution series. Cell viability was determined by using a CellTiter-Glo® assay (CTG).
Figure 2A:
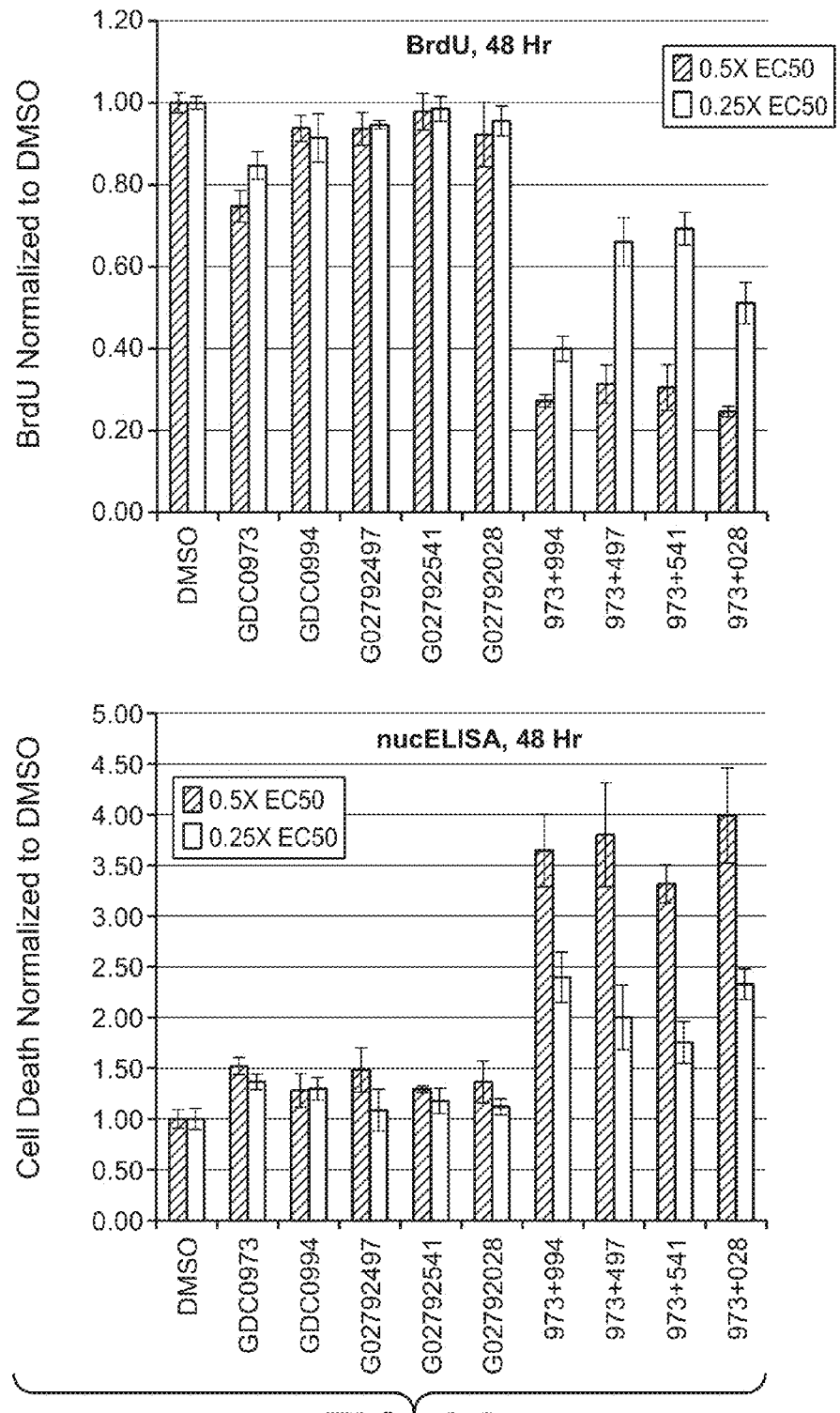
FIG. 2A and FIG. 2B show cell proliferation of and extent of apoptosis in A549 non-small cell lung cancer (NSCLC) cells when dosed with doses of GDC-0994, Ib, Ic or Id and GDC-0973 individually or dosed with doses of GDC-0994, Ib, Ic or Id combined with GDC-0973. Cell proliferation was determined using a BrdU assay. Apoptosis was measured using a nucELISA assay.
Figure 2B:
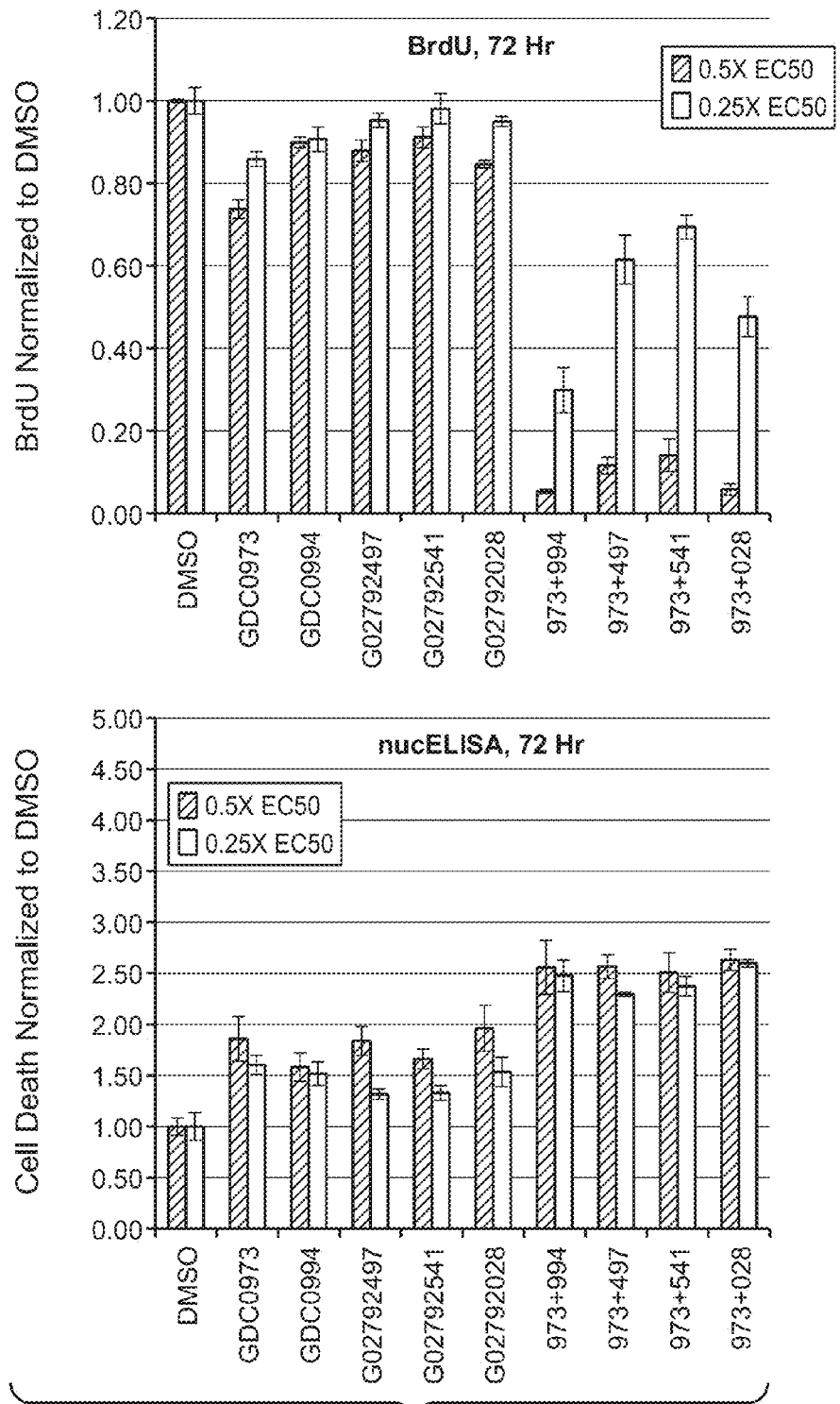

The synergy was observed with all MEKi inhibitors co-administered with GDC-0994 (FIG. 12) and with all ERKi co-administered with GDC-0973 (FIG. 1)

One aspect of the invention provides for a method for the treatment of cancer in a patient in need thereof using combination therapy comprising administration of a MEK inhibitor, and an ERK inhibitor or a pharmaceutically acceptable salt of either.

In one embodiment, the MEK inhibitor of the combination therapy is either GDC-0973 or GDC-0623. GDC-0973 and GDC-0623 are potent and highly selective small molecule allosteric inhibitors of MEK 1/2, the kinases that activate ERK 1/2 Inhibition of MEK 1/2 is a strategy to control the growth of tumors that are dependent on aberrant signaling in the MEK/ERK pathway. Preclinical studies have demonstrated that both inhibitors are effective in inhibiting the growth of tumor cells bearing activating B-RAF mutations that are associated with many tumor types, with GDC-0973 showing more activity in this model. Preclinical studies have demonstrated that both inhibitors are effective in inhibiting the growth of tumor cells bearing activating Ras mutations that are associated with many tumor types, with GDC-0623 showing more activity in this model. Administration of the MEK inhibitor is combined with an ERK inhibitor. In a specific embodiment the ERK inhibitor is selected from Ia, Ib, Ic or Id.

The combination therapy would also serve to prevent or delay the inherent or acquired resistance attributable to activation of the RAS/RAF/MEK/ERK pathway observed with MEK inhibition and to prevent or delay inherent or acquired resistance mediated via RAS pathway activation.

The combination may be employed in combination with chemotherapeutic agents for the treatment of a hyperproliferative disease or disorder, including tumors, cancers, and neoplastic tissue, along with pre-malignant and non-neoplastic or non-malignant hyperproliferative disorders.

In certain embodiments, a combination is combined in a dosing regimen as combination therapy, with another compound that has anti-hyperproliferative properties or that is useful for treating the hyperproliferative disorder. The additional compound of the dosing regimen preferably has complementary activities to the combination, and such that they do not adversely affect each other. Such compounds may be administered in amounts that are effective for the purpose intended.

In one embodiment, the therapeutic combination is administered by a dosing regimen wherein the therapeutically effective amount of a MEK inhibitor compound (such as GDC-0973 or GDC-0623), or a pharmaceutically acceptable salt thereof is administered in a range from once daily for three weeks or every three days (Q3D) for three weeks and the therapeutically effective amount of a compound of formula Ia-Id once daily for three weeks.

The combination therapy may be administered as a simultaneous or sequential regimen. When administered sequentially, the combination may be administered in two or more administrations. The combined administration includes co-administration, using separate formulation, and consecutive administration in either order, wherein preferably there is a time period while both (or all) active agents simultaneously exert their biological activities.

In one embodiment of the invention the hyperproliferative disorder is cancer.

In another embodiment of the invention the cancer expresses mutant KRAS.

In another embodiment of the present invention the MEKi is GDC-0973 (II).

In another embodiment of the present invention the MEKi is GDC-0623 (IIa).

In another embodiment of the present invention the MEKi is GSK-1120212 (trametinib).

In another embodiment of the present invention the MEKi is AZD-6244 (selumetinib).

In another embodiment of the present invention the MEKi is BAY 86-9766 (refametinib).

In another embodiment of the present invention the ERKi is a compound of formula Ia.

In another embodiment of the present invention the ERKi is a compound of formula Ib.

In another embodiment of the present invention the ERKi is a compound of formula Ic.

In another embodiment of the present invention the ERKi is a compound of formula Id.

In another embodiment of the present invention there is provided a method for treating cancer with a combination of a MEKi and an ERKi wherein said cancer or hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma.

In another embodiment of the present invention there is provided a method for treating cancer with a combination of a MEKi and an ERKi wherein said cancer is selected from the group consisting of colorectal cancer, lung cancer, mesothelioma, breast cancer, pancreatic cancer, glioma, gastric cancer, renal cancer, ovarian cancer, endometrial cancer, bladder cancer and head and neck cancer.

In another embodiment of the present invention there is provided a method for treating cancer with a combination of the MEKi II and the ERKi Ia wherein said cancer or hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma.

In another embodiment of the present invention there is provided a method for treating cancer with a combination of the MEKi II and the ERKi Ia wherein said cancer is selected from the group consisting of colorectal cancer, lung cancer, mesothelioma, breast cancer, pancreatic cancer, glioma, gastric cancer, renal cancer, ovarian cancer, endometrial cancer, bladder cancer and head and neck cancer.

In another embodiment of the present invention there is provided a method for treating cancer with a combination of the MEKi IIa and the ERKi Ia wherein said cancer or hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, heptoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma.

In another embodiment of the present invention there is provided a method for treating cancer with a combination of the MEKi IIa and the ERKi Ia wherein said cancer is selected from the group consisting of colorectal cancer, lung cancer, mesothelioma, breast cancer, pancreatic cancer, glioma, gastric cancer, renal cancer, ovarian cancer, endometrial cancer, bladder cancer and head and neck cancer.

In another embodiment there is provided a method for treating cancer with a combination of II or IIa and Ia are administered concurrently.

In another embodiment there is provided a method for treating cancer with a combination of II or IIa and Ia are administered sequentially.

In another embodiment of the present invention there is provide a composition for the treatment of cancer containing of GDC-0973 (II) or GDC-0623 (IIa), or a pharmaceutically acceptable salt thereof and ERK inhibitor selected from Ia, Ib, Id, or Id or a pharmaceutically acceptable for the treatment of cancer.

In another embodiment of the present invention there is provide a composition for the treatment of cancer containing of GDC-0973 (II) or a pharmaceutically acceptable salt thereof and ERK inhibitor selected from Ia, Ib, Id, or Id or a pharmaceutically acceptable for the treatment of cancer.

In another embodiment of the present invention there is provide a composition for the treatment of cancer containing of GDC-0973 (II) or GDC-0623 (IIa), or a pharmaceutically acceptable salt thereof and ERK inhibitor selected from Ia, Ib, Id, or Id or a pharmaceutically acceptable for the treatment of cancer wherein said cancer is selected from the group consisting of colorectal cancer, lung cancer, mesothelioma, breast cancer, pancreatic cancer, glioma, gastric cancer, renal cancer, ovarian cancer, endometrial cancer, bladder cancer and head and neck cancer.

In another embodiment of the present invention there is provide a composition for the treatment of cancer containing of GDC-0973 (II), or a pharmaceutically acceptable salt thereof and ERK inhibitor selected from Ia, Ib, Id, or Id or a pharmaceutically acceptable for the treatment of cancer wherein said cancer is selected from the group consisting of colorectal cancer, lung cancer, mesothelioma, breast cancer, pancreatic cancer, glioma, gastric cancer, renal cancer, ovarian cancer, endometrial cancer, bladder cancer and head and neck cancer.

In another embodiment of the present invention there is provided the use of a MEKi of formula II and an ERK inhibitor of formula Ia for the manufacture of a medicament for the treatment of cancer or a hyperproliferative disease.

In another embodiment of the present invention there is provided the use of a MEKi of formula II and an ERK inhibitor of formula Ia for the manufacture of a medicament for the treatment of cancer.

In another embodiment of the present invention there is provided a kit comprising GDC-0973 or GDC-0623, or a pharmaceutically acceptable salt thereof, GDC-0994, or a pharmaceutically acceptable salt thereof, a container, and a package insert or label indicating the administration GDC-0973 or GDC-0623, or a pharmaceutically acceptable salt thereof; and GDC-0994, for treating cancer.

In another embodiment of the present invention there is provided a product comprising GDC-0973 or GDC-0623, or a pharmaceutically acceptable salt thereof and GDC-0994, or a pharmaceutically acceptable salt, as a combined preparation for separate, simultaneous or sequential use in the treatment of cancer.

In another embodiment of the present invention there is provided a combination of GDC-0973 or GDC-0623, or a pharmaceutically acceptable salt thereof and ERK inhibitor for the therapeutic treatment of cancer.

In another embodiment of the present invention there is provided a method of treating cancer or a hyperproliferative disease wherein GDC-0973, or a pharmaceutically acceptable salt thereof, or GDC-0623, or a pharmaceutically acceptable salt thereof, and GDC-0994 are each administered in an amount from about 1 mg to about 1000 mg per unit dosage form.

In another embodiment of the present invention there is provided a method of treating cancer or a hyperproliferative disease wherein GDC-0973, or a pharmaceutically acceptable salt thereof, is administered at a dose of 60 mg, on days 1-21 of a 28 day cycle, and GDC-0994, or a pharmaceutically acceptable salt thereof is administered in an amount from about 1 mg to about 1000 mg per unit dosage form.

In another embodiment of the present invention there is provided a method for treating cancer or a hyperproliferative disease wherein with a combination of GDC-0973 and GDC-0994 wherein GDC-0973 is administered once or twice daily for three weeks of a four week cycle at a dose between 3 mg/kg and 7.5 mg/kg and GDC-0994 is administered once or twice daily for three weeks of a four week cycle at a dose between 25 mg/kg and 75 mg/kg.

Pharmaceutical Compositions

Pharmaceutical compositions or formulations of the present invention include combinations as described herein.

The compound or a pharmaceutically acceptable salt thereof may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the herein-described method of treating a patient by administering a pharmaceutical composition of the present invention is also intended to encompass the administration of the bulk composition and individual dosage units.

The pharmaceutically acceptable salts of the compounds are formulated in accordance with standard pharmaceutical practice for use in a therapeutic combination for therapeutic treatment of hyperproliferative disorders (such as cancer, such as triple negative breast cancer) in mammals including humans (such as human males or females). The invention provides a pharmaceutical composition comprising a combination as described herein in association with one or more pharmaceutically acceptable carrier, glidant, diluent, or excipient.

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The pharmaceutical composition (or formulation) for administration may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical formulations will be dosed and administered in a fashion, e.g., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

Formulations of combinations suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount GDC-0973 and GDC-0623, or a pharmaceutically acceptable salt thereof and an ERK inhibitor of formula Ia-Id. The amount of GDC-0973 or GDC-0623 and Ia-Id, or a pharmaceutically acceptable salt thereof may be formulated in a pill, capsule, solution or suspension as a combined formulation. Alternatively, the combination may be formulated separately in a pill, capsule, solution or suspension for administration by alternation.

Formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablet excipients of a pharmaceutical formulation may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tableting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or *acacia*; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation include Tween® 60, Span® 80, cetostearyl alcohol, benzyl alcohol, myristyl alcohol, glyceryl mono-stearate and sodium lauryl sulfate.

Aqueous suspensions of the pharmaceutical formulations contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum *acacia*, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The amount(s) of active ingredient(s) that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Articles of Manufacture

In another embodiment of the invention, an article of manufacture, or "kit", containing a combination useful for the treatment of the diseases and disorders described above is provided. In one embodiment, the kit comprises a container and a combination described herein.

The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a combination, or a formulation thereof, which is effective for treating the condition and may have a sterile access port (for example, the container may be an intravenous solution bag or a vial having a stopper pierceable by a hypodermic injection needle). The label or package insert indicates that the composition is used for treating the condition of choice, such as cancer. In one embodiment, the label or package inserts indicates that the composition comprising the combination can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the combination, and, if present, the second pharmaceutical formulation. For example, if the kit comprises a first composition comprising GDC-0973 or GDC-0623, or a pharmaceutically acceptable salt thereof and a second pharmaceutical formulation comprising an ERK inhibitor, or a pharmaceutically acceptable salt thereof, the kit may further comprise directions for the simultaneous, sequential or separate administration of the first and second pharmaceutical compositions to a patient in need thereof.

In another embodiment, the kits are suitable for the delivery of solid oral forms of a combination, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with GDC-0973 or GDC-0623, (b) a second container with ERK inhibitor or a pharmaceutically acceptable salt thereof contained therein, and (c) a third container with a third pharmaceutical formulation contained therein, wherein the third pharmaceutical formulation comprises another compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of GDC-0973 or GDC-0623, or a pharmaceutically acceptable salt thereof and an ERK inhibitor, or a pharmaceutically acceptable salt thereof, or a pharmaceutically acceptable salt thereof the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

REFERENTIAL EXAMPLE 1

(S)-(3,4-difluoro-2-((2-fluoro-4-iodophenyl)amino)phenyl)(3-hydroxy-3-(piperidin-2-yl)azetidin-1-yl)methanone (GDC-0973)

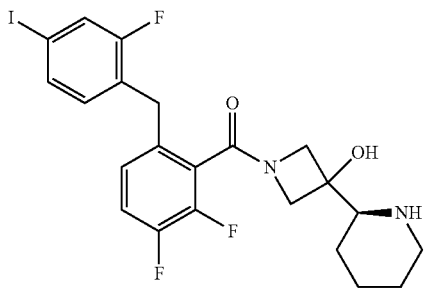 [SMILES: O=C(c1c(Cc2ccc(I)cc2F)ccc(F)c1F)N1CC(O)([C@@H]2CCCCN2)C1]

The title compound cane be prepared as described by K. D. Rice, et al., *ACS Med. Chem. Lett.* 2012 3:416-421 in Example 22 of WO2007044515 or, alternatively, as described as described by K. D. Rice et al., Novel Carboxamide-Based Allosteric MEK inhibitors: Discovery and Optimization Efforts toward XL518 (GDC-0973), *Med. Chem. Lett.* 2012 3:416.

REFERENTIAL EXAMPLE 2

5-[(2-fluoro-4-iodophenyl)amino]-N-(2-hydroxyethoxy)-imidazo[1,5-a]pyridine-6-carboxamide

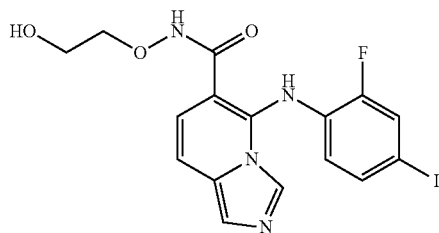

The title compound can be prepared as described in Example 5 of WO2009085983.

REFERENTIAL EXAMPLE 3

(S)-1-(1-(4-chloro-3-fluorophenyl)-2-hydroxyethyl)-4-(2-((1-methyl-1H-pyrazol-4-yl)amino)pyrimidin-4-yl)pyridin-2(1H)-one

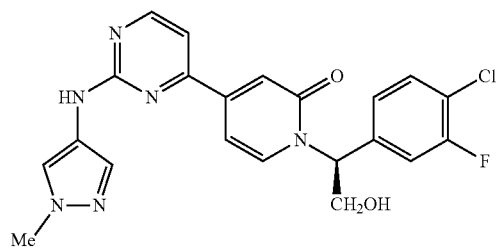 [SMILES: Cn1cc(Nc2nccc(-c3ccn([C@H](CO)c4ccc(Cl)c(F)c4)c(=O)c3)n2)cn1]

4-(2-(methylthio)pyrimidin-4-yl)pyridin-2(1H)-one

Step 1: A suspension of 4-bromo-2-(methylthio)pyrimidine (7.00 g, 34.1 mmol), 2-fluoropyridin-4-ylboronic acid (5.05 g, 35.8 mmol), $Na_2CO_3$ (10.9 g, 102 mmol) and $Pd(dppf)Cl_2 \cdot CH_2Cl_2$ (1.40 g, 1.71 mmol) in dioxane/$H_2O$ (100 mL; 1:1) was heated to 85° C. under an Ar balloon for 2 h. The reaction mixture was cooled to RT and concentrated. The residue was diluted with ethyl acetate (200 mL) and water (100 mL). The layers were separated, and the aqueous layer was extracted with ethyl acetate (1X). The organics were dried, filtered and concentrated. The crude product was purified via column chromatography, eluting with hexanes/ethyl acetate (3:1) to give 4-(2-fluoropyridin-4-yl)-2-(methylthio)pyrimidine (6.83 g, 90%) as a solid. $^1$H NMR (400 MHz, $(CD_3)_2SO$) δ 8.85 (d, J=5.2 Hz, 1H), 8.46 (d, J=5.2 Hz, 1H), 8.11 (m, 1H), 7.96 (d, J=5.2 Hz, 1H), 7.92 (s, 1H), 2.62 (s, 3H); m/z (APCI-pos) M+1=222.1.

Step 2: A suspension of 4-(2-fluoropyridin-4-yl)-2-(methylthio)pyrimidine (6.83 g, 30.9 mmol) in 2N HCl (100 mL) was heated to reflux for 2 hours. The reaction mixture was cooled to room temperature and placed in an ice bath. The pH was adjusted to about 7 with 2N NaOH (about 100 mL). The resulting solids were collected by filtration, washed with water and dried to give 4-(2-(methylthio)pyrimidin-4-yl)pyridin-2(1H)-one (5.07 g) as a solid. This material was placed in the thimble of a Soxhlet apparatus and was attached to a 1 L flask charged with ethyl acetate (500 mL). The material was continuously extracted for 3 days. The resulting white precipitate from the ethyl acetate layer was collected by filtration (3.3 grams, 49% yield). $^1$H NMR (400 MHz, $(CD_3)_2SO$) δ 11.85 (br, s, 1H), 8.75 (d, J=5.0 Hz, 1H), 7.79 (d, J=5.0 Hz, 1H), 7.54 (d, J=7.0 Hz, 1H), 7.13 (s, 1H), 6.86 (d, J=7.0 Hz, 1H), 2.58 (s, 3H); m/z (APCI-pos) M+1=220.0.

(R)-2-(tert-butyldimethylsilyloxy)-1-(4-chloro-3-fluorophenyl)ethyl methanesulfonate Step 1: Sodium hydride (8.549 g, 213.7 mmol, 60% suspension in mineral oil) was added portionwise to a cold (0° C.) solution of 4-chloro-3-fluorobenzaldehyde (26.07 g, 164.4 mmol) and methyltriphenylphosphonium bromide (70.48 g, 197.3 mmol) in THF (400 mL). The reaction mixture was allowed to warm up to RT overnight. The solids were removed by filtration, and the filter cake was washed with ether. The filtrate was concentrated (water bath about 20° C.), and the residue was suspended in hexanes and stirred for 30 minutes. The solids (mostly $PPh_3O$) were removed by filtration, and the filter cake was washed with hexanes. The filtrate was concentrated, and the crude product was purified by column chromatography, eluting with hexanes/ethyl acetate (25:1) to give 1-chloro-2-fluoro-4-vinylbenzene (12.1 g, 47%) as an oil. $^1$H NMR (400 MHz, $CDCl_3$) δ 7.33 (m, 1H), 7.18 (m, 1H), 7.10 (m, 1H), 6.63 (m, 1H), 5.74 (d, J=17.4 Hz, 1H), 5.32 (d, J=10.8 Hz, 1H).

Step 2: 1-Chloro-2-fluoro-4-vinylbenzene (12.1 g, 77.3 mmol) was added to a cold (0° C.) solution of AD-mix-β (108 g, 139 mmol) in t-BuOH/$H_2O$ (600 mL; 1:1), and the mixture was allowed to warm up to RT overnight. The next day, the reaction was placed in an ice bath and quenched with solid $Na_2SO_3$ (114 g). The mixture was stirred for 1 h and then extracted with ethyl acetate (3×500 mL). The combined organics were dried, filtered and concentrated to give (R)-1-(4-chloro-3-fluorophenyl)ethane-1,2-diol as an oil. The crude product was used in the next step without purification.

Step 3: Imidazole (13.1 g, 193 mmol) was added to a cold (0° C.) solution of (R)-1-(4-chloro-3-fluorophenyl)ethane-1,2-diol (14.7 g, 77.1 mmol) in DCM (100 mL), followed by TBSCl (12.8 g, 84.8 mmol). The reaction mixture was stirred at 0° C. for 1 hour and then quenched with water (50 mL). The layers were separated, and the organics were dried, filtered and concentrated. The crude product was purified via column chromatography, eluting with hexanes/ethyl acetate (100:1) to give (R)-2-(tert-butyldimethylsilyloxy)-1-(4-chloro-3-fluorophenyl)ethanol (11.0 g, 47% over two steps). $^1$H NMR (400 MHz, CDCl$_3$) δ 7.36 (m, 1H), 7.20 (m, 1H), 7.08 (m, 1H), 4.71 (m, 1H), 3.75 (m, 1H), 3.49 (m, 1H), 2.96 (d, J=2.6 Hz, 1H), 0.90 (s, 9H), 0.07 (s, 3H), 0.06 (s, 3H).

Step 4: Triethylamine (2.09 mL, 15.0 mmol) was added to a cold (0° C.) solution of (R)-2-(tert-butyldimethylsilyloxy)-1-(4-chloro-3-fluorophenyl)ethanol (3.05 g, 10.0 mmol) in DCM (100 mL), followed by methanesulfonyl chloride (0.929 mL, 12.0 mmol). The reaction mixture was stirred at 0° C. for 30 minutes and then quenched with water (50 mL). The layers were separated, and the organic layer was washed with saturated NaHCO$_3$, dried, filtered and concentrated to give the crude product. The crude product was purified via column chromatography, eluting with hexanes/ethyl acetate (25:1) to give (R)-2-(tert-butyldimethylsilyloxy)-1-(4-chloro-3-fluorophenyl)ethyl methanesulfonate (3.80 g, 99%) as an oil. $^1$H NMR (400 MHz, CDCl$_3$) δ 7.42 (m, 1H), 7.20 (m, 1H), 7.12 (m, 1H), 5.50 (m, 1H), 3.91 (m, 1H), 3.80 (m, 1H), 2.98 (s, 3H), 0.88 (s, 9H), 0.05 (s, 3H), 0.04 (s, 3H).

(S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one Step 1: 1.0M KHMDS (5.09 mL, 5.09 mmol) as a solution in THF was added to a cold (0° C.) suspension of 4-(2-(methylthio)pyrimidin-4-yl)pyridin-2(1H)-one (0.93 g, 4.24 mmol) in THF (20 mL). The reaction mixture was stirred at 0° C. for 10 minutes before (R)-2-(tert-butyldimethylsilyloxy)-1-(4-chloro-3-fluorophenyl)ethyl methanesulfonate (2.44 g, 6.36 mmol) was added as a solution in THF (5 mL). The reaction was heated to reflux for 30 h and then cooled to RT and concentrated. The residue was taken up in ethyl acetate (200 mL) and washed with water. The organics were dried, filtered and concentrated. The crude product was purified via column chromatography, eluting with hexanes/ethyl acetate (4:1) to give (S)-1-(2-(tert-butyldimethylsilyloxy)-1-(4-chloro-3-fluorophenyl)ethyl)-4-(2-(methylthio)pyrimidin-4-yl)pyridin-2(1H)-one (1.35 g, 63%) as a solid. $^1$H NMR (400 MHz, CDCl$_3$) δ 8.66 (d, J=5.0 Hz, 1H), 7.43 (m, 2H), 7.34 (d, J=5.0 Hz, 1H), 7.32-7.28 (m, 2H), 7.16 (m, 1H), 6.85 (m, 1H), 6.24 (m, 1H), 4.35 (m, 1H), 4.23 (m, 1H), 2.65 (s, 3H), 0.88 (s, 9H), 0.03 (s, 3H), −0.03 (s, 3H); m/z (APCI-pos) M+1=506.1, 508.1.

Step 2: mCPBA (7.1 g, 29 mmol) was added to a cold (0° C.) solution of (S)-1-(2-(tert-butyldimethylsilyloxy)-1-(4-chloro-3-fluorophenyl)ethyl)-4-(2-(methylthio) pyrimidin-4-yl)pyridin-2(1H)-one (5.8 g, 11 mmol) in DCM (100 mL), and the mixture was stirred for 2 hours. The reaction mixture was washed with saturated Na$_2$S$_2$O$_3$ (1X), NaHCO$_3$ (1x), dried, filtered, and evaporated. The crude product was purified via column chromatography, eluting with hexanes/ethyl acetate (1:1) to give (S)-1-(2-(tert-butyldimethylsilyloxy)-1-(4-chloro-3-fluorophenyl)ethyl)-4-(2-(methylsulfonyl)pyrimidin-4-yl)pyridin-2(1H)-one (5.5 g, 89%) as a solid. $^1$H NMR (400 MHz, CDCl$_3$) δ 9.06 (d, J=5.2 Hz, 1H), 7.91 (d, J=5.4 Hz, 1H), 7.55 (d, J=7.4 Hz, 1H), 7.43 (m, 1H), 7.32 (d, J=2.4 Hz, 1H), 7.27 (m, 1H), 7.15 (m, 1H), 6.93 (m, 1H), 6.22 (m, 1H), 4.35 (m, 1H), 4.24 (m, 1H), 3.45 (s, 3H), 0.88 (s, 9H), 0.03 (s, 3H), −0.03 (s, 3H); m/z (APCI-pos) M+1=538.1, 540.0.

REFERENTIAL EXAMPLE 4

4-[3-[[ethyl(dimethyl)silyl]methyl]-[1,2,4]triazolo[4,3-a]pyridin-7-yl]-N-(2-methylpyrazol-3-yl)pyrimidin-2-amine

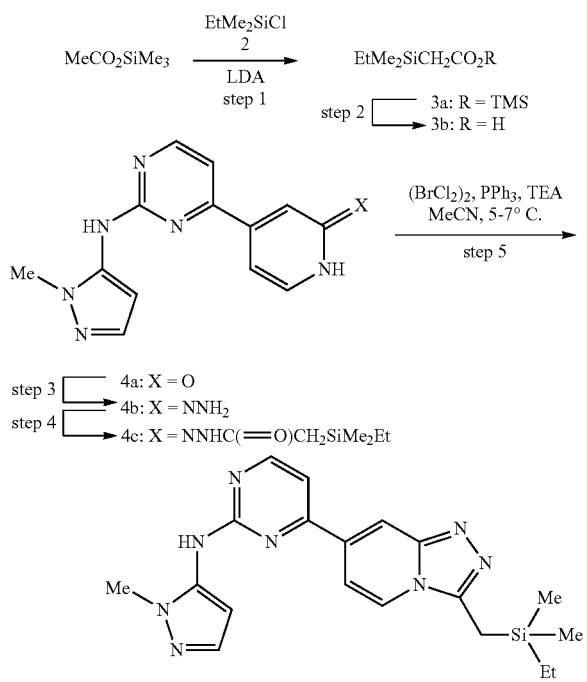

2-(ethyldimethylsilyl)acetic acid (4)

To a solution of THF (40 mL) and LDA (8.8 ml, 17.5 mmol) was added cooled to −78° C. was added slowly trimethylsilylacetate (2.0 g, 15.1 mmol). The mixture was stirred at −78° C. for 2 h. Chloro(ethyl)dimethylsilane (2.1 g, 17.5 mmol) was added and the resulting solution was stirred for 2 h. The mixture was quenched with brine (10 ml) and then HCl (10 ml, 1N) was added slowly and the resulting solution extracted with MTBE (3×20 mL). The combined extracts were dried, concentrated and the residue purified by SiO2 chromatography eluting with EtOAc/hexane (1:10) to afford 1.0 g (45%) of 2-(ethyldimethylsilyl)acetic acid as colorless oil. $^1$H NMR (400 MHz, CDCl3) δ =1.80 (s, 1 H), 0.84 (t, J=8.0 Hz, 3H), 0.50 (q, J=8.0 Hz, 2H), 0.00 (s, 6H).

(Z)-2-(ethyldimethylsilyl)-N'-(4-(2((1-methyl-1H-pyrazol-5-yl)amino)pyrimidin-4-yl)pyridin-2(1H)-ylidene)acetohydrazide (7)

To 2-chloro-1-methylpyridin-1-ium (1.36 g, 5.3 mmol) in DCM (10 ml) was added (Z)-4-(2-hydrazono-1,2-dihydropyridin-4-yl)-N-(1-methyl-1H-pyrazol-5-yl)pyrimidin-2-amine (1.3 g, 4.6 mmol) and 2-(ethyldimethylsilyl)acetic acid (0.67 g, 4.6 mmol) were added followed by tributylamine (1.96 g, 10.6 mmol). The mixture was stirred at 60-80° C. for 1 h. The mixture was concentrated, purified on a SiO2 column eluting with EtOAc then DCM/MeOH (10:1) to afford (Z)-2-(ethyldimethylsilyl)-N'-(4-(2-((1-methyl-1H-pyrazol-5-yl)amino)pyrimidin-4-yl)pyridin-2(1H)-ylidene) acetohydrazide (1.1 g, 44%) as a yellow solid.

4-(3-((ethyldimethylsilyl)methyl)-[1,2,4]triazolo[4,3-a]pyridin-7-yl)-N-(1-methyl-1H-pyrazol-5-yl)pyrimidin-2-amine (GNT_D379_285-1)

A flask was charged with (Z)-2-(ethyldimethylsilyl)-N'-(4-(2-((1-methyl-1H-pyrazol-5-yl)amino)pyrimidin-4-yl)pyridin-2(1H)-ylidene)acetohydrazide (7) (500 mg, 1.22 mmol) and 1,2-dibromotetrachloroethane (793 mg, 2.44 mmol) then CH$_3$CN (20 ml) was added, followed by portionwise addition of PPh3 (798 mg, 3.0 mmol). The mixture was stirred at 5-7° C. for 1 h then TEA (1.0 ml) was added dropwise and the resulting mixture stirred at 5-7° C. for 2 h. The mixture was filtered, the filtrate was concentrated, purified SiO$_2$ chromatography eluting with EtOAc then MeOH/DCM (1:20) to afford the crude (200 mg) which was washed with EtOAc and MeOH (three times) to afford 4-(3-((ethyldimethylsilyl)methyl)-[1,2,4]triazolo[4,3-a]pyridin-7-yl)-N-(1-methyl-1H-pyrazol-5-yl)pyrimidin-2-amine (GNT_D379_285-1) (73 mg, 15%) as a white solid.

$^1$H NMR (400 MHz, DMSO-d6) δ=9.58 (s, 1H), 8.60 (d, J=5.2 Hz, 1H), 8.56 (d, J=7.6 Hz, 1H), 8.50 (s, 1H), 7.68 (d, J=5.2 Hz, 1H), 7.59 (d, J=7.6 Hz, 1H), 7.40 (s, 1H), 6.31 (s, 1H), 3.71 (s, 3H), 2.60 (s, 2H), 0.88 (t, J=8.0 Hz, 3H), 0.58 (t, J=8.0 Hz, 2H), 0.05 (s, 6H); MS [M+H]$^+$=392.19.

REFERENTIAL EXAMPLE 4

4-[3-(2-methylbutyl)triazolo[1,5-a]pyridin-6-yl]-N-(2-methylpyrazol-3-yl)pyrimidin-2-amine

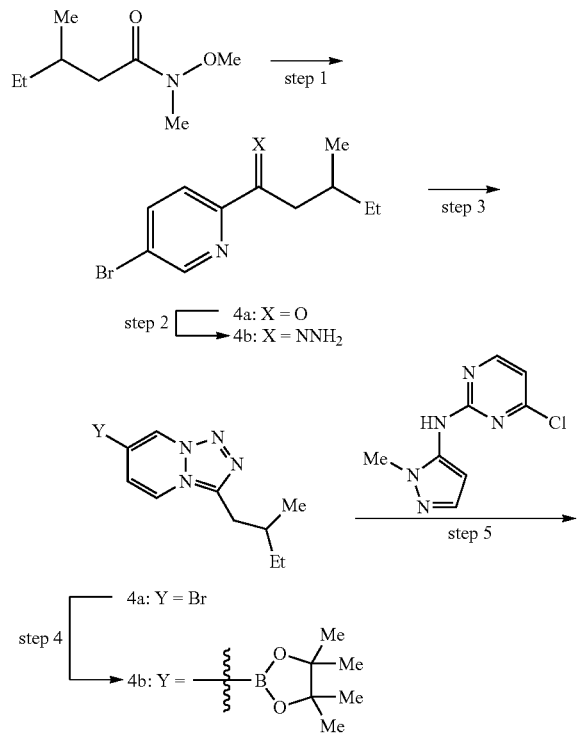

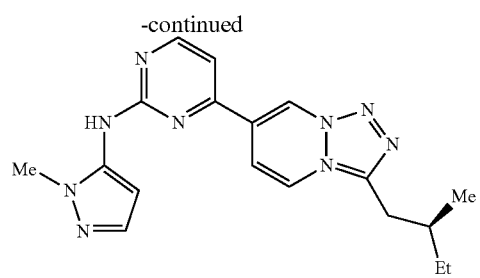

1-(5-bromopyridin-2-yl)-3-methylpentan-1-one

A solution of 2,5-dibromopyridine (3.72 g, 15.8 mmol) in toluene (30 ml) was cooled to −40° C., and n-BuLi (6.32 mL, 15.8 mmol) was added dropwise. The mixture was stirred at −40° C. for 1 h and then a solution of N-methoxy-N, 3-dimethylpentanamide (2.1 g, 13.2 mmol, CASRN 1051483-44-3) and toluene (5 mL) added dropwise. The mixture was stirred for another 2 h, then quenched with aqueous NH$_4$Cl (aq) and extracted with EtOAc (2×50 mL). The organic phase was dried, concentrated and purified on a SiO2 column eluting with EtOAc/hexane (1:10) to afford the title compound (2 g, 59%) as a yellow oil.

$^1$H NMR (400 MHz, MeOH-d$_4$) δ: 8.75 (d, J=2.0 Hz, 1H), 8.13 (dd, J=8.4, 2.4 Hz, 1H), 7.92 (d, J=8.4 Hz, 1H), 3.17-3.12 (m, 1H), 2.98-2.92 (m, 1H), 2.02-2.00 (m, 1H), 1.41-1.21 (m, 2H), 0.93-0.89 (m, 6H).

(Z)-5-bromo-2-(1-hydrazono-3-methylpentyl)pyridine 1-(5-bromopyridin-2-yl)-3-methylpentan-1-one (2.0 g, 6.2 mmol) was dissolved in MeOH (50 mL) and NH$_2$NH$_2$ (5 ml) was added. The mixture was stirred at reflux for 4 h. 2N NaOH (5 mL) and H$_2$O (20 mL) was added and the resulting mixture extracted with EtOAc (3×50 mL). The organic phase was dried (Na$_2$SO$_4$), filtered and concentrated. The residue was used directly in the next step without further purification: MS [M+H]$^+$=269.7.

6-bromo-3-(2-methylbutyl)-[1,2,3]triazolo[1,5-a]pyridine

To a solution of crude (Z)-5-bromo-2-(1-hydrazono-3-methylpentyl)pyridine (1.9 g, 7.1 mmol) in CHCl$_3$ (30 mL) was added active MnO$_2$ (3 g, 35.3 mmol). The mixture was heated to reflux and stirred for 16 h. The mixture was filtered, the filtrate was concentrated and purified SiO2 chromatography to afford 1.6 g of the title compound: MS [M+H]$^+$=267.7.

3-(2-methylbutyl)-6-(4,4,5,5-tetramethyl-1,3,2-dioxaborolan-2-yl)-[1,2,3]triazolo[1,5-a]pyridine A solution of 6-bromo-3-(2-methylbutyl)-[1,2,3]triazolo[1,5-a]pyridine (0.8 g, 3 mmol), 4,4,4',4',5,5,5',5'-octamethyl-2,2'-bi(1,3,2-dioxaborolane) (838 mg, 3.3 mmol), KOAc (294 mg, 9 mmol) and Pd(dppf)Cl$_2$ (329 mg, 0.45 mmol) in dioxane (30 mL) was heated at 100° C. with stirring under N$_2$ for 3 h. Then crude product was used in the next step without further purification: MS [M+H]$^+$=233.7.

N-(1-methyl-1H-pyrazol-5-yl)-4-(3-(2-methylbutyl)-[1,2,3]triazolo[1,5-a]pyridin-6-yl)pyrimidin-2-amine (GNT_D379_260)

To the product crude boronic ester was added 4-chloro-N-(1-methyl-1H-pyrazol-5-yl)pyrimidin-2-amine (755 mg, 3.6 mmol), Pd(dppf)Cl$_2$ (329 mg, 0.45 mmol) and Cs$_2$CO$_3$ (2.9 g, 9 mmol) and water H$_2$O (5 mL). The mixture was stirred at 100° C. for 4 h. The mixture was filtered. The filtrate was concentrated and purified on a SiO2 column via column on silica gel and followed by Pre-HPLC to afford the title compound (250 mg). $^1$H NMR (400 MHz, MeOH-d$_4$) δ: 9.58 (s, 1H), 8.54 (d, J=5.2 Hz, 1H), 8.00-7.90 (m, 2H), 7.50-7.47 (m, 2H), 6.36 (d, J=2 Hz, 1H), 3.77 (s, 3H), 3.03-2.99 (m, 1H), 2.87-2.81 (m, 1H), 1.91 (m, 1H), 1.46-1.42 (m, 1H), 1.28-1.24 (m, 1H), 0.98-0.91 (m, 6H); MS [M+H]$^+$=362.9.

The (S) enantiomer was obtained by SFC chromatography on a chiral support.

$^1$H NMR (400 MHz, MeOHl-d$_4$) δ: 9.58 (s, 1H), 8.53 (d, J=5.2 Hz, 1H), 8.00-7.90 (m, 2H), 7.50-7.46 (m, 2H), 6.36 (d, J=2 Hz, 1H), 3.77 (s, 3H), 3.05-2.99 (m, 1H), 2.87-2.81 (m, 1H), 1.91 (m, 1H), 1.46-1.27 (m, 1H), 1.26-1.24 (m, 1H), 0.98-0.91 (m, 6H).

REFERENTIAL EXAMPLE 5

4-[3-[2-(4-chlorophenyl)-2-methoxy-ethyl]-[1,2,4]triazolo[4,3-b]pyridazin-7-yl]-N-(2-methylpyrazol-3-yl)pyrimidin-2-amine

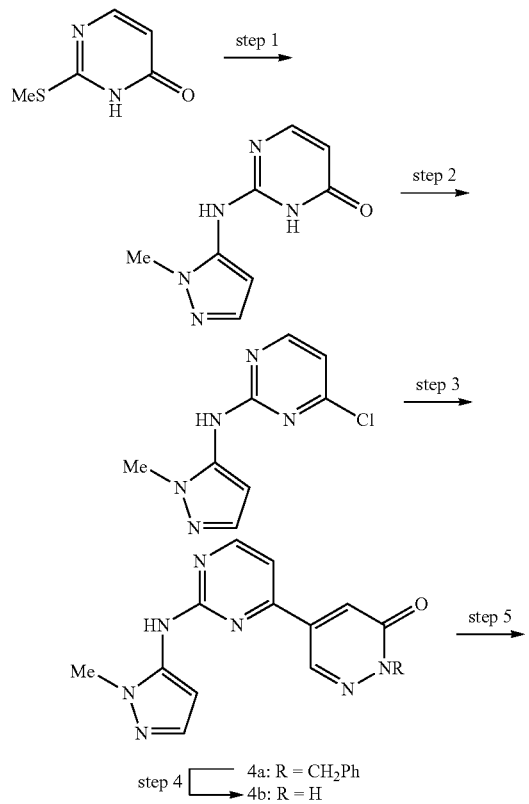

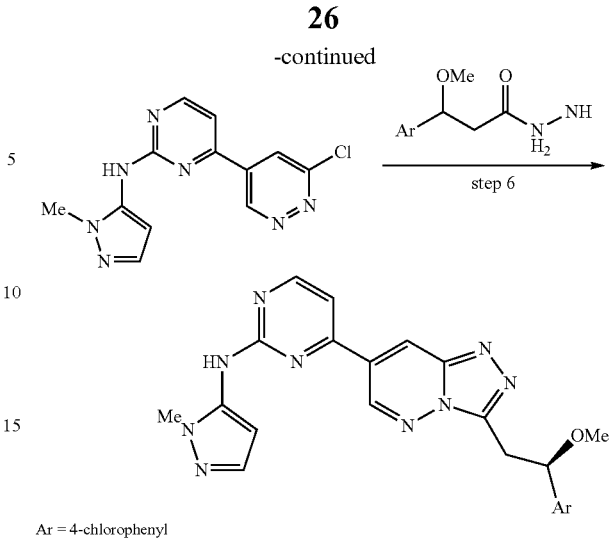

Ar = 4-chlorophenyl

Step 1: 2-((1-methyl-1H-pyrazol-5-yl)amino)pyrimidin-4(3H)-one (6)

A mixture of 2-(methylthio)pyrimidin-4(3H)-one (10 g, 70 mmol, CASRN 5751-20-2) and 1-methyl-1H-pyrazol-5-amine (10 g, 103 mmol) in Me$_3$CCO$_2$H (50 g) was heated to 160° C. for 48 h. The mixture was allowed to cool to 40-50° C. and DCM (30 ml) was added. After stirring for 10 min the solution was diluted with n-hexane (200 mL1) which formed a red slurry. The mixture was allowed to stand for 0.5 h after which the top clear organic phase was decanted. The red slurry was dissolved in DCM (50 ml) and concentrated under reduced pressure to give crude product 2 (16.5 g) which was used in the next step without any purification.

Step 2: 4-chloro-N-(1-methyl-1H-pyrazol-5-yl)pyrimidin-2-amine (7)

To a solution of 2-((1-methyl-1H-pyrazol-5-yl)amino)pyrimidin-4(3H)-one (16.5 g, crude) in MeCN (200 ml) was added POCl$_3$ (30 ml, 0.33 mol). The mixture was heated to reflux for 15 min. The mixture was quenched by ice-water (100 g), and pH was adjusted to 10 by Na$_2$CO$_3$ powder. The mixture was extracted with EtOAc (3×100 mL), dried (Na$_2$SO$_4$), filtered and concentrated under reduced pressure to give crude product. The crude product was purified by SiO$_2$ chromatography eluting with petroleum ether/EtOAc (1:1) to afford 7.5 g (51% for 2 steps) of the title compound. 1H NMR (MeOH-d4, 400 MHz) δ: 8.30 (d, J=5.2, 1H), 7.42 (d, J=1.6, 1H), 6.90 (d, J=5.2, 1H), 6.28 (d, J=1.6, 1H), 3.72 (s, 3H)

Step 3: 2-benzyl-5-(2-((1-methyl-1H-pyrazol-5-yl)amino)pyrimidin-4-yl)pyridazin-3(2H)-one (9)

To a solution of 4-chloro-N-(1-methyl-1H-pyrazol-5-yl)pyrimidin-2-amine (25.0 g, 119 mmol) in dioxane (300 mL) was added Me$_3$SnSnMe$_3$ (46.9 g, 143.11 mmol) and Pd(PPh$_3$)$_4$ (13.8 g, 11.93 mmol), the mixture was heated at 125° C. under N$_2$ atmosphere for 3 h. To the above solution was added 2-benzyl-5-iodopyridazin-3(2H)-one 3 (44.7 g, 143.1 mmol, CASRN 825633-93-0), LiCl (10.1 g, 238.5 mmol), CuI (11.4 g, 59.6 mmol) and Pd(PPh$_3$)$_4$ (13.8 g, 11.93 mmol). The mixture was heated at 125° C. under N$_2$ atmosphere for 16 h. The mixture was cooled to RT and filtered through Celite®. The filter cake was washed with DCM (3×200 mL). The combined with DCM solutions were concentrated, purified by SiO2 chromatography eluting with a MeOH/DCM gradient (1-5% MeOH) to give the compound d (34 g, 84%) as a yellow solid.

Step 4: 5-(2-((1-methyl-1H-pyrazol-5-yl)amino) pyrimidin-4-yl)pyridazin-3(2H)-one (10)

To a solution of anhydrous toluene (500 mL) and 2-benzyl-5-(2-((1-methyl-1H-pyrazol-5-yl)amino)pyrimidin-4-yl)pyridazin-3(2H)-one (34 g, 94.6 mmol) was added AlCl$_3$ (63 g, 473 mmol). The mixture was heated at 120° C. under N$_2$ atmosphere for 1 h. The mixture was cooled to RT and the top clear layer was decanted. The remaining solid was added to ice water (200 g), and stirred at RT until the initial solid decomposed and yellow solid appeared. The solid was filtered and washed with ice water (3×100 mL). After drying ca. 35 g crude yellow solid product was obtained.

Step 5: 4-(6-chloropyridazin-4-yl)-N-(1-methyl-1H-pyrazol-5-yl)pyrimidin-2-amine To a stirred POCl$_3$ (200 mL) was added 5-(2-((1-methyl-1H-pyrazol-5-yl)amino)pyrimidin-4-yl)pyridazin-3(2H)-one (10) (35 g crude, 0.13 mol) at RT. The mixture was heated at 80° C. for 2 h. The mixture was concentrated to dryness, dissolved with CHCl$_3$ (200 mL) and then poured into ice water (500 g) with stirring. The resulting mixture was adjusted to pH ca. 8. The mixture was extracted with DCM (5×300 mL). The combined organic layer was concentrated and purified by SiO2 chromatography eluting with a petroleum ether/EtOAc gradient (1 to 50% EtOAc) to afford 13 g (47% over 2 steps) of the title compound as a yellow solid. $^1$H NMR (DMSO-d$_6$, 400 MHz) δ: 9.80 (s, 1H), 9.74 (s, 1H), 8.70 (d, J=4.8, 1H), 8.44 (s, 1H), 7.72 (d, J=5.2, 1H), 7.38 (s, 1H), 6.29 (s, 1H), 3.68 (s, 3H).

Step 6: 4-(3-(2-(4-chlorophenyl)-2-methoxyethyl)-[1,2,4]triazolo[4,3-b]pyridazin-7-yl)-N-(1-methyl-1H-pyrazol-5-yl)pyrimidin-2-amine To the stirred solution of 4-(6-chloropyridazin-4-yl)-N-(1-methyl-1H-pyrazol-5-yl)pyrimidin-2-amine (200 mg, 0.758 mmol) in IPA (3 mL) was added 3-(4-chlorophenyl)-3-methoxypropanehydrazide (200 mg, 0.834 mmol), and methane sulphonic acid (1.2 mg, 1.6 mmol). The reaction mixture was stirred at 100° C. for 3 h. The solvent was evaporated to dryness and purified by preparative HPLC (FA) to afford 40 mg (7%) of the desired product. $^1$H NMR (400 MHz, MeOH-d4) δ: 9.24 (s, 1H), 8.88 (s, 1H), 8.63 (d, J=5.2, 1H), 7.63 (d, J=5.2, 1H), 7.51 (d, J=2.0, 1H), 7.36 (s, 4H), 6.39 (s, 1H), 4.63 (s, 1H), 3.82 (s, 3H), 3.81-3.74 (m, 1H), 3.59-3.54 (m, 1H), 3.20 (s, 3H); MS [M+H]$^+$=461.9.

The (R)-4-(3-(2-(4-chlorophenyl)-2-methoxyethyl)-[1,2,4]triazolo[4,3-b]pyridazin-7-yl)-N-(1-methyl-1H-pyrazol-5-yl)pyrimidin-2-amine enantiomer was resolved by SFC to afford the desired product (13.8 mg). $^1$H NMR (400 MHz, DMSO-d$_6$) δ 9.70 (s, 1H), 9.19 (s, 1H), 9.00 (d, J=2, 1H), 8.67 (d, J=4.8, 1H), 7.23 (d, J=4.8, 1H), 7.42-7.35 (m, 4H), 6.33 (s, 1H), 4.93-4.89 (m, 2H), 3.73 (s, 3H), 3.72-3.64 (m, 1H), 3.50-3.44 (m, 1H), 3.10 (s, 3H)); MS [M+H]$^+$=461.9.

BIOLOGICAL EXAMPLE 1

Cell Culture and Viability Assays

For CellTiterGlo (Promega): A549 cells were plated in normal growth medium (Roswell Park Memorial Institute 1640 (RPMI 1640) media with 10% fetal bovine serum, 2 mM/L-glutamine and 100 units/mL of penicillin and streptomycin).at 1500 cells per well in a 384-well clear-bottom black plate. The following day, compounds were serially diluted 1:2 starting at indicated concentrations, then added to cells in quadruplicates. 96 hours following compound addition, CellTiter-Glo Luminescent Cell Viability reagent was added per manufacturer's protocol.

For BrdU ELISA (Roche): A549 cells were plated in normal growth medium at 3000 cells per well in a 96-well clear-bottom black plate. The following day, compounds were added in triplicates at indicated concentrations based on CTG results. 48 and 72 hours following compound addition, BrdU Cell Proliferation Chemiluminescent ELISA was performed according to manufacturer's protocol.

For Cell Death nucELISA (Roche): A549 cells were plated in normal growth medium at 3000 cells per well in a 96-well clear-bottom black plate. The following day, compounds were added in triplicates at indicated concentrations based on CTG results. 48 and 72 hours following compound addition, Cell Death Detection ELISA$^{PLUS}$ was performed according to manufacturer's protocol.

BIOLOGICAL EXAMPLE 2

Tumor Xenograft Models

Cultured NCI-H520.X1 and EBC1 cells were removed from culture, suspended in Hank's buffered saline solution (HBSS), mixed 1:1 with Matrigel (BD Biosciences, USA), and implanted subcutaneously into the right flank of naïve female NCR nude mice (Taconic Farms, Hudson, N.Y.). Mice with tumors of a mean volume of approximately 250 mm$^3$ were grouped into treatment cohorts of 10 mice each. Mice received 5% sucrose only or 5% sucrose plus 1 mg/ml doxycycline (Clontech, Mountain View, Calif.) for control and knockdown cohorts, respectively. All water bottles were changed 3 times per week. Body weights and tumor volume measurements (as obtained by length and width measurements with calipers) were taken twice per week during the study. All experimental procedures conformed to the guiding principles of the American Physiology Society and were approved by Genentech's Institutional Animal Care and Use Committee. Tumor volumes were calculated by the following formula: Tumor Volume=0.5*(a*b$^2$), where 'a' is the largest tumor diameter and 'b' is the perpendicular tumor diameter. Tumor volume results are presented as mean tumor volumes±the standard error of the mean (SEM). Percent growth inhibition (% INH) at the end of study (EOS) was calculated as % INH=100 [(EOS Vehicle-EOS Treatment)/(EOS Vehicle)]. Data analysis and generation of p-values using the Dunnett t-test was done using JMP software (SAS Institute, Cary, N.C.).

Ia was prepared as a solution at various concentrations (expressed as free-base equivalents) in 40% PEG400 (polyethylene glycol 400)/60% [10% HP-β-CD (hydroxypropyl-β-cyclodextrin)]. The vehicle control was 40% PEG400/60% (10% HP-β-CD) or MCT. II was prepared as a suspension at various concentrations in methyl cellulose tween (MCT). Ia, II, and vehicle control dosing solutions were prepared once a week for three weeks. The formulations were mixed well by vortexing before dosing. Test articles were stored in a refrigerator set to maintain a temperature range of 4° C.-7° C.

BIOLOGICAL EXAMPLE 3

Genetically Modified Mouse Models

We obtained mice from the following institutions: Kras$^{LSL-G12D}$ mice were obtained from from Tyler Jacks (Massachusetts Institute of Technology), p16/p19$^{fl/fl}$ mice were obtained from Anton Berns (NKI, The Netherlands), p53frt/frt mice were obtained from Exelixis, Inc. and Pdxl-Cre mice were obtained from Andy Lowy (University of Ohio). Equal numbers of male and female animals were used for experimental cohorts, dosing commenced following confirmation of tumor burden via either ultrasound imaging for PDAC or microCT for NSCLC model. The animals were dosed and monitored according to guidelines from the Institutional Animal Care and Use Committee (IACUC) at Genentech, Inc. All chosen dosing regimens were well tolerated in the GEMMs. Noninvasive imaging and assessment of overall survival were performed as previously described in {Singh:2010hv} In the GEM models, cobimetinib and Ia were dosed at 5 mg/kg and 60 mg/kg by oral gavage (PO), daily (QD).

Statistical analyses from data shown as Kaplan-Meier survival estimates and imaging data sets were carried out as previously described (M. Singh et al., *Nature Biotechnol.*, 2010, 28(6):585-593). GEM model tumor samples were collected and stored in RNALater (Qiagen, Valencia, Calif.). Total RNA was extracted with RNeasy Plus Mini kit (Qiagen) following manufacturer's instructions. RNA quantity was determined using Naondrop (Thermo Scientific, Waltham, Mass.).

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A method of treating colorectal cancer, the method comprising administering to a mammal in need thereof a therapeutically effective amount of a combination of cobimetinib, or a pharmaceutically acceptable salt thereof, and (S)-1-(1-(4-chloro-3-fluorophenyl)-2-hydroxyethyl)-4-(2-((1-methyl-1H-pyrazol-5-yl)amino)pyrimidin -4-yl)pyridin-2(1H)-one, or a pharmaceutically acceptable salt thereof, either as a combined formulation or by alternation.

2. A method of treating lung cancer, the method comprising administering to a mammal in need thereof a therapeutically effective amount of a combination of cobimetinib, or a pharmaceutically acceptable salt thereof, and (S)-1-(1-(4-chloro-3 -fluorophenyl)-2-hydroxyethyl)-4-(2-((1-methyl-1H-pyrazol-5 --yl)amino)pyrimidin -4-yl)pyridin-2(1H)-one, or a pharmaceutically acceptable salt thereof, either as a combined formulation or by alternation.

3. The method of claim 2 wherein the lung cancer is non-small cell lung cancer.

4. A method of treating pancreatic cancer, the method comprising administering to a mammal in need thereof a therapeutically effective amount of a combination of cobimetinib, or a pharmaceutically acceptable salt thereof, and (S)-1-(1-(4-chloro-3-fluorophenyl)-2-hydroxyethyl)-4-(2 ((1-methyl-1H-pyrazol-5-yl)amino)pyrimidin-4-yl)pyridin-2(1H)-one, or a pharmaceutically acceptable salt thereof, either as a combined formulation or by alternation.

5. The method of any one of claims 1 to 4 wherein the cancer is associated with a KRAS mutation.

6. The method of any one of claims 1 to 4 wherein the mammal is a human.

7. The method of any one of claims 1 to 4 wherein the administration is by alternation.

8. The method of any one of claims 1 to 4 wherein the administration is by combined formulation.

* * * * *